(12) United States Patent
Hostetter et al.

(10) Patent No.: US 6,676,943 B1
(45) Date of Patent: Jan. 13, 2004

(54) **HUMAN COMPLEMENT C3-DEGRADING PROTEIN FROM *STREPTOCOCCUS PNEUMONIAE***

(75) Inventors: Margaret K. Hostetter, New Haven, CT (US); Gary Dunny, St. Paul, MN (US); Lakshmi S. Nandiwada, Mendota Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/403,422

(22) PCT Filed: Apr. 24, 1998

(86) PCT No.: PCT/US98/08281
§ 371 (c)(1),
(2), (4) Date: Oct. 19, 1999

(87) PCT Pub. No.: WO98/48022
PCT Pub. Date: Oct. 29, 1998

Related U.S. Application Data

(60) Provisional application No. 60/044,316, filed on Apr. 24, 1997.

(51) Int. Cl.[7] .............................................. A61K 39/02
(52) U.S. Cl. ................................ 424/190.1; 424/184.1; 424/185.1; 424/234.1; 424/237.1; 424/244.1; 424/69.1; 424/320.1; 536/23.1; 536/23.7; 530/324; 530/350; 530/380
(58) Field of Search ............................... 530/300, 350, 530/380, 324; 424/184.1, 185.1, 190.1, 234.1, 237.1, 244.1, 94.1; 514/1; 536/23.1, 23.2; 435/69.1, 320.1

(56) References Cited

U.S. PATENT DOCUMENTS

| | | |
|---|---|---|
| 4,902,506 A | 2/1990 | Anderson et al. |
| 5,360,897 A | 11/1994 | Anderson et al. |
| 5,476,929 A | 12/1995 | Briles et al. |
| 5,510,264 A | 4/1996 | Van Alstyne et al. |
| 5,614,382 A | 3/1997 | Metcalf |

FOREIGN PATENT DOCUMENTS

| | | |
|---|---|---|
| EP | 0 622 081 | 11/1994 |
| EP | 0 687 688 | 12/1995 |
| WO | WO 93/10238 | 5/1993 |
| WO | WO 95/06732 | 3/1995 |
| WO | WO 95/14712 | 6/1995 |
| WO | WO 95/31548 | 11/1995 |
| WO | WO 96/05859 | 2/1996 |
| WO | WO 96/16082 | 5/1996 |
| WO | WO 97/26008 | 7/1997 |
| WO | WO 97/41151 | 11/1997 |
| WO | WO 98/18930 | 5/1998 |
| WO | WO 98/18931 | 5/1998 |
| WO | WO 98/21337 | 5/1998 |
| WO | WO 98/48022 | 10/1998 |
| WO | WO 99/15675 | 1/1999 |
| WO | 00/37105 | 6/2000 |

OTHER PUBLICATIONS

US 6,159,469, 12/2000, Choi et al. (withdrawn)
Havarstein et al. PNAS vol. 92, pp. 11140–11144, Nov. 1995.*
Angel et al (Journal of Infectious Diseases vol. 170(3) pp. 600–608, 1994.*
Nandiwada et al. "Genetic analysis of a C3 degrading proteinase in *Spreptococcus pneumoniae*". 96th General Meeting of the American Society for Microbiology. New Orleans, Louisiana, USA. Abstracts on the General Meeting of the American Society for Micribiology. Abstract B–134, May 1996.*
Hostetter et al., "Interactions of C3 with bacterial pathogens," Grant Abstract, Grant No. 1R01AI24162–01A1 [online]. National Institute of Allergy and Infectious Diseases, National Institutes of Health, project dates Jul. 01, 1987— Jun. 30, 1990 [retrieved on May 01, 2001]. Retrieved from the Internet: URL: http://commons.cit.nih.gov/crisp_historical/crisp_lib.getdoc?textkey=3136924&p_grant_num=1R01AI24162–01A1&p_query=& ticket=76732&p_audit_session_id =446565&p_keywords=.
Angel et al., "Functional Characteristics of a C3–Cleaving Proteinase from *Streptococcus pneumoniae*," Abstract 949, 103rd Ann. Meeting American Pediatric Society and 62nd Ann. Meeting Society for Pediatric Research, Washington, May 3–6, 1993, *Pediatr. Res.*, 33(4, Part 2):161A (1993).
Angel et al., "Degradation of C3 by *Streptococcus pneumoniae*," *J. Infect. Dis.*, 170:600–608 (1994).
Baquero et al., "A review of antibiotic resistance patterns of *Streptococcus pneumoniae* in Europe," *J. Antimicrob. Chemother.*, 28(Suppl. C):31–38 (1991).
Bendel et al., "Distinct Mechanisms of Epithelial Adhesion for *Candida albicans* and *Candida tropicalis*. Identification of the Participating Ligands and Development of Inhibitory Peptides," *J. Clin. Invest.*, 92: 1840–1849 (1993).
Berry et al., "Cloning and Nucleotide Sequence of the *Streptococcus pneumoniae* Hyaluronidase Gene and Purification of the Enzymes from Recombinant *Escherichia coli*," *Infect. Immun.*, 62(3):1101–1108 (1994).
Birnboim et al., "A rapid alkaline extraction procedure for screening recombinant plasmid DNA," *Nuc. Acids Res.*, 7(6):1513–1523 (1979).

(List continued on next page.)

*Primary Examiner*—Lynette R. F. Smith
*Assistant Examiner*—Robert A. Zeman
(74) *Attorney, Agent, or Firm*—Mueting Raasch & Gebhardt

(57) ABSTRACT

The present invention relates to the identification and use of a family of human complement C3-degrading proteinases expressed by *S. pneumoniae*. The proteinase has a molecular weight of about 24 kD to about 34 kD as determined on a 10% SDS polyacrylamide gel. A preferred proteinase of this invention includes the amino acid sequence of SEQ ID NO:2.

50 Claims, 2 Drawing Sheets

OTHER PUBLICATIONS

Boulard, "Degradation of bovine C3 by serine proteases from parasites *Hypoderma lineatum* (Diptera, Oestridae)," Abstract, *Vet. Immunol. Immunopathol.,* 20(4):387–398, (1989).

Cannon et al., "Immunogenicity of C3 Binding Protein of *Streptococcus pneumoniae*," Abstract and Poster, MARC/MBRS National Meeting, Miami (Nov. 13–17, 1996).

Centers for Disease Control, Immunization Practices Advisory Commitee, "Update: Pneumococcal Polysaccharide Vaccine Usage—United States," *Morbidity and Mortality Weekly Report,* 33(20)273–276, 284 (1984).

Charriaut–Marlangue et al., "Identification of P–57, a Serine Proteinase, from Human Erythrocyte Membranes, which Cleaves Both Chains of Human Third Component (C3) of Complement," *Biochem. Biophysical Res. Comm.,* 140(3):1113–1120 (1986).

Cheng et al., "A C–3 binding protein in *Streptococcus pneumoniae*," Abstract B–478, p. 110, Abstracts of the 97$^{th}$ Annual Meeting of the American Society for Microbiology, Miami Beach, (May 4–8, 1997).

Clark et al., "Role of Ammonia in Progressive Interstitial Nephritis," *Am. J. Kid. Dis.,* 17(5, Suppl. 1):15–19 (1991).

Clark et al., "Hyperosmolality impairs ammonia–mediated inflammation: implications for the renal medulla," *Am. J. Physiol.,* 263(1)R148–R155 (1992).

Connor et al., "Chapter 9: Human Immunodeficiency Virus Infections in Infants and Children," *Current Topics in AIDS: vol. 1*, Gottlieb et al., eds., John Wiley & Sons., Bath, Great Britain, Title page, publication page, table of contents and pp. 185–209 (1987).

Cundell et al., "Peptide Permeases from *Streptococcus pneumoniae* Affect Adherence to Eucaryotic Cells," *Infect. Immun.,* 63(7):2493–2498 (1995).

Czinn et al., "Protection of germ–free mice from infection by *Helicobacter felis* after active oral or passive IgA immunization," *Vaccine,* 11(6):637–642 (1993).

Filice et al., "Bacteremia in Charleston County, South Carolina," *Am. J. Epidemiol.,* 123(1):128–136 (1986).

Giebink et al., "Bacterial and Polymorphonuclear Leukocyte Contribution to Middle Ear Inflammation in Chronic Otitis Media with Effusion," *Ann. Otol. Rhinol. Laryngol.,* 94(4):398–402 (1985).

Giebink et al., "Pneumococcal Capsular Polysaccharide–Meningococcal Outer Membrane Protein Complex Conjugate Vaccines: Immunogenicity and Efficacy in Experimental Pneumococcal Otitis Media," *J. Invest. Dis.,* 167(2):347–355 (1993).

Gilmore et al., "An iC3b Receptor on *Candida albicans*: Structure, Function, and Correlates for Pathogenicity," *J. Infect. Dis.,* 157(1):38–46 (1988).

Gordon et al., "Amidation of C3 at the Tiolester Site: Description of a New Inflammatory Mediator," Abstract, 42$^{nd}$ Annual Meeting of the American Federation for Clinical Research, Oct. 31–Nov. 2, 1984, *Clin. Res.,* 32(4):758A (1984).

Gordon et al., "Amidation of C3 at the Thiolester Site: Stimulation of Chemiluminescence and Phagocytosis by a New Inflammatory Mediator," *J. Immunol.,* 134(5):3339–3345 (1985).

Gordon et al., "Reaction of Ammonia with Complement Component C3: Binding to the CR1 Receptor and Stimulation of Phagocytic Oxidative Metabolism," Abstract, 42$^{nd}$ Annual National Meeting of the American Federation for Clinical Research, Washington, May 3–6, *Clin. Res.,* 33(2):377A (1985).

Gordon et al., "Complement and Host Defence Against Microorganisms," *Pathology,* 18(4):365–375 (1986).

Gordon et al., "Ligand–receptor Interactions in the Phagocytosis of Virulent *Streptococcus pneumoniae* by Polymorphonuclear Leukocytes," *J. Infect. Dis.,* 154(4):619–626 (1986).

Gordon et al, "Characteristics of iC3b binding to human polymorphonuclear leucocytes," *Immunology,* 60:553–558 (1987).

Gordon et al., "Analysis of C3 Deposition and Degradation on Bacterial Surfaces after Opsonization," *J. Infect. Dis.,* 157(4):697–704 (1988).

Gyllensten et al., "Generation of single stranded DNA by the polymerase chain reaction and its application ot direct sequencing of the HLA–DQA Locus," *Proc. Nat. Acad. Sci. USA,* 85(20):7652–7656 (1988).

Harlow et al., *Antibiodies: A Laboratory Manual,* Cold Spring Harbor Laboratory Press, Cold Spring Harbor, NY: title page, publisher's page, and table of contents, 9 pages (1988).

Håvarstein et al., "An unmodified heptadecapeptide pheromone induces competence for genetic transformation in *Streptococcus pneumoniae*," *Proc. Natl. Acad. Sci. USA,* 92(24):11140–11144 (1995).

Henwick et al., "Specificity of three anti–complement factor 3 monoclonal antibodies," *J. Immunol. Methods,* 153(1–2):173–184 (1992).

Hillenkamp et al, "Mass Spectrometry of Peptides and Proteins by Matrix–Assisted Ultraviolet Laser Desorption/Ionization," *Methods in Enzymology: Mass Spectrometry, vol. 193*, McCloskey, ed., Academic Press, Inc., San Diego, Title page, publication page and pp. 280–295 (1990).

Holmgren et al., "Mucosal Immunity: Implications for Vaccine Development," *Immunobiol.,* 184(2/3):157–179 (1992).

Hostetter et al., "Binding of C3b proceeds by a transesterification reaction at the thiolester site," *Nature,* 298(5869):72–75 (1982).

Hostetter et al., "Nucleophilic Attack on Complement Protein C3 in Chronic Renal Failure," Abstract 1174, 75$^{th}$ Ann. Meeting Am. Soc. of Biological Chemists and 68$^{th}$ Ann. Meeting Am. Assoc. of Immunologists, St. Louis, Mo., Jun. 3–7, 1984, *Federation Proceedings,* 43(6):1617 (1984).

Hostetter et al., "The Biochemistry of Opsonization: Central Role of the Reactive Thiolester of the Third Component of Complement," *J. Infect. Dis.,* 150(5):653–661 (1984).

Hostetter et al., "Amidation of C–3 by Erythrocytes," Abstract 103, 11$^{th}$ International Complement Workshop, Miami, Nov. 3–5, 1985, *Complement,* 2(1):37 (1985).

Hostetter et al., "Amidation of C–3 by Mucoid *Pseudomonas aeruginosa*; a Mechanism for Opsonic Failure and Phagocytic Activation in the Cystic Fibrosis Lung," Abstract, 43$^{rd}$ Ann. National Meeting of the American Federation for Clinical Research, Washington, May 2–5, 1986, *Clin. Res.,* 34(2):520A (1986).

Hostetter, "Serotypic Variations Among Virulent Pneumococci in Deposition and Degradation of Covalently Bound C3b: Implications for Phagocytosis and Antibody Production," *J. Infect. Dis.*, 153(4):682–693 (1986).

Hostetter et al., "Biochemistry of C3 and Related Thiolester Proteins in Infection and Inflammation," *Rev. Infect. Dis.*, 9(1):97–109 (1987).

Hostetter et al., "Humans C3 with Disrupted Thiolester is Mitogenic for Normal Human B Lymphocytes," Abstract 106, 13th International Complement Workshop, San Diego, Sep. 10–15, 1989, *Complement and Inflammation*, 6(5) 347–348 (1989).

Hostetter et al., "The Erythrocyte as an Instigator of Inflammation. Generation of Amidated C3 by Erythrocyte Adenosine Deaminase," *J. Clin. Invest.*, 84:665–671 (1989).

Hostetter et al, "The iC3b Receptor of *Candida albicans*: Subcellular Localization and Modulation of Receptor Expression by Glucose," *J. Infect. Dis.*, 161(4):761–768 (1990).

Hostetter, "Perspectives in Diabetes: Handicaps to Host Defense. Effects of Hyperglycemia on C3 and *Candida albicans*," *Diabetes*, 39(3):271–275 (1990).

Hostetter, "Function of Integrin Analogues in Adhesion," *J. Mycol. Med.*, 2(1):14–18 (1992).

Hostetter, "C3–Cleaving Proteinase from *Streptococcus pneumoniae*," Abstract, 32nd Ann. Meeting of the American Society for Clinical Nutrition, Baltimore, Apr. 30–May 2, 1992, *Clin. Res.*, 40(2):214A (1992).

Hostetter, "Chapter 7: C3 and C4 as opsonins in natural immunity," *The Natural Immune System: Humoral Factor*, Sim et al., eds.; IRL Press, Oxford, Title page, publication page, table of contents and pp. 177–208 (1993).

Hostetter, "The third component of complement: New functions for an old friend," 66th Ann. Meeting Central Society for Clinical Research, Chicago, Nov. 3–5, 1993, *J. Lab. Clin. Med.*, 122(5):491–496 (1993).

Hostetter et al., "Virulence and Host Response: Prospects for Control with Conjugate Pneumococcal Vaccines," Abstract 577, Ann. Meeting American Society for Microbiology, San Francisco, Sep. 17–20, 1995, *Abstracts of the 35th Interscience Conference on Antimicrobial Agents and Chemotherapy*, p. 364 (1995).

Hostetter, "Opsonic and Nonopsonic Interactions of C3 with *Streptococcus pneumoniae*," *Microbial Drug Resistance*, 5(2):85–89 (1999).

Janoff et al., "Pneumococcal Disease During HIV Infection. Epidemiologic, Clinical, and Immunologic Perspectives," *Ann. Intern. Med.*, 117(4):314–324 (1992).

Jasin, "Human Heat Labile Opsonins: Evidence for their Mediation Via the Alternate Pathway of Complement Activation," *J. Immunol.*, 109(1):26–31 (1972).

Johnston et al., "The Enhancement of Bacterial Phagocytosis by Serum: The Role of Complement Components and Two Cofactors," *J. Exp. Med.*, 129(5):1275–1290 (1969).

Kreig et al., "Nucleic Acid Sequencing and Mutagenesis: Double–Stranded DNA Template Preparation," *Promega Protocols and Applications Guide*, Promega Corp., Madison, Wisconsin, Title page, table of contents and pp. 106–108 (1991).

Kyte et al., "A Simple Method for Displaying the Hydropathic Character of a Protein," *J. Mol. Biol.*, 157(1):105–132 (1982).

Laemmli, "Cleavage of Structural Proteins during the Assembly of the Head of Bacteriophage T4," *Nature*, 227(5259):680–685 (1970).

Lecroisey et al., "Hypodermin B, a trypsin–related enzyme from the insect *Hypoderma lineatum*. Comparison with hypodermin A and *Hypoderma collagenase*, two serine proteinases from the same source," Abstract, *Eur. J. Biochem.*, 134(2)261–67 (1983).

Lee et al., "Protection of infant mice from challenge with *Streptococcus pneumoniae* type 19F by immunization with a type 19F polysaccharide–pneumolysoid conjugate," *Vaccine*, 12(10):875–878 (1994).

Loewenson et al., "Functional Implications of Site–specific Glucosylation of Human C3 in Hyperglycemia," Abstract, 45th Annual National Meeting of the American Federation for Clinical Research, Washington, Apr. 29–May 2, 1988, *Clin. Res.*, 36(3):462A (1988).

Macrina et al., "Novel shuttle plasmid vehicles for Escherichia–Streptococcus transgeneric cloning," *Gene*, 25:145–150 (1983).

Madsen et al., "Production of IL–8 by Pulmonary Epithelial Cells in Response to Secreted Proteins of *S. pneumoniae*," Abstract 736, Ann. Meeting American Pediatric Society–Society for Pediatric Research, Washington, DC, May 2–6, 1997, *Pediatr. Res.* 41(4, part 2):125A (1997).

Mann et al., "The Third Component of Complement: Covalent Attachment of a Radioactive Sugar to the Labile Binding Site of C–3 via the Alternative Pathway," *J. Immunol.*, 126(6):2370–2372 (1981).

Masi et al., "Evaluation of Recombinant C3 Degrading Protein from *S. pneumoniae* as a Vaccine Candidate," Abstract, Second International Symposium of Pneumococcal Diseases, Sun City, Northwest Province, South Africa (Mar. 19–23, 2000).

Matsudaira, "Sequence from Picomole Quantities of Proteins Electroblotted onto Polyvinylidene Difluoride Membranes," *J. Biol. Chem.*, 262(21):10035–10038 (1987).

Martin et al., "Relatedness of penicillin–binding protein 1a genes from different clones of penicillin–resistant *Streptococcus pneumoniae* isolated in South Africa and Spain," *EMBO J.*, 11(11):3831–3836 (1992).

McDaniel et al., "Molecular localization of variable and conserved regions of pspA and identification of additional pspA homologous sequences in *Streptococcus pneumoniae*," *Microb. Pathogen.* 13:261–269 (1992).

McDaniel et al., "Localization of protection–eliciting epitopes on PspA of *Streptococcus pneumoniae* between amino acid residues 192 and 260," *Microb. Pathogen.*, 17:323–337 (1994).

McGhee et al., "The mucosal immune system: from fundamental concepts to vaccine development," *Vaccine*, 10(2):75–88 (1992).

Michael et al., "C3 Synthesis by Malignant Epithelium: A Potential Autocrine Stimulus for Cellular Proliferation," Abstract, Joint Meeting Central Society for Clin. Res., Am. Fed. For Clin. Res., Midwest Soc. For Pediatric Res., and Central Region Society for Investigative Dermatology, Chicago, Nov. 4–6, 1992, *Clin. Res.*, 40(3):693A (1992).

Michael et al., "Components of an Autocrine Loop for C3 Synthesis by Epithelial Cells," Abstract, 32nd Annual Meeting of the American Society for Clinical Nutrition, Baltimore, Apr. 30–May 2, 1992, Abstract, *Clin. Res.*, 40(2):379A (1992).

Michael et al., "Expression of CD21 and synthesis of its ligands by HeLa cells after growth in serum–free medium," 68th Ann. Meeting Central Society for Clinical Research, Chicago, Sep. 28–30, 1995, *J. Lab. Clin. Med.*, 125(1):102–112 (1995).

Morrison et al., "Isolation and Characterization of Three New Classes of Transformation–Deficient Mutants of *Streptococcus pneumoniae* That Are Defective in DNA Transport and Genetic Recombination," *J. Bacteriol.*, 156(1):281–290 (1983).

Nakamura et al., eds., *Immunochemical Assays and Biosensor Technology for the 1990's*, American Society fo Microbiology, Washington, D.C., Title page, publication page, and table of contents, 4 pgs. (1992).

Nandiwada et al., "Genetic Analysis of a C3 Degrading Proteinase in *Streptococcus pneumoniae*," Abstract B–134, 96th General Meeting of the American Society for Microbiology, New Orleans, May 19–23, p 177 (1996).

Nath et al, "Pathophysiology of Chronic Tubulo–Interstitial Disease in Rats. Interactions of Dietary Acid Load, Ammonia, and Complement Component C3," *J. Clin. Invest.*, 76(2):667–675 (1985).

Nath et al., "Ammonia–complement interaction in the pathogenesis of progressive renal injury," *Kidney Int.*, 36(Suppl. 27):S52–S54 (1989).

Pearce et al., "Genetic identification of exported proteins in *Streptococcus pneumoniae*," *Molecular Microbiol.*, 9(5):1037–1050 (1993).

Reed et al., "Cleavage of C3 by a Neutral Cysteine Proteinase of *Entamoeba histolytica*," *J. Immunol.*, 143(1):189–195 (1989).

Sambrook et al., *Molecular Cloning, A Laboratory Manual*, second edition, Cold Spring Harbor Laboratory Press, Cold Spring Harbor, NY, Title page, publication page and table of contents, 30 pgs. (1989).

Sampson et al., "Cloning and Nucleotide Sequence Analysis of psaA, the *Streptococcus pneumoniae* Gene Encoding a 37–Kilodalton Protein Homologous to Previously Reported *Streptococcus sp.* Adhesins," *Infect. Immun.*, 62(1):319–324 (1994).

Schägger et al., "Tricine–Sodium Dodecyl Sulfate–Polyacrylamide Gel Electrophoresis for the Separation of Proteins in the Range from 1 to 100 kDa," *Anal. Biochem.*, 166:368–379 (1987).

Sedegah et al., "Protection against malaria by immunization with plasmid DNA encoding Circumsporozoite protein," *Proc. Natl. Acad. Sci. USA*, 91(21):9866–9870 (1994).

Sicard, "A New Synthetic Medium for Diplococcus Pneumoniae, and its Use for the Study of Reciprocal Transformations at the amiA Locus," *Genetics*, 30(1):31–44 (1964).

Smith et al., "Characterization of a Pneumococcal Surface Protein that Binds Complement Protein C3 and its Role in Adhesion," Abstract D–122, 98th General Meeting of the American Society for Microbiology, Atlanta, May 17–21, 1998, *Abstracts of the General Meeting of the American Society for Microbiology*, p. 233 (1998).

Smith et al., "Factors Modulating Pneumococcal Adhesion," Abstract 1097, Ann. Meeting American Pediatric Society–Society for Pediatric Research, Washington, DC, May 6–10, 1996, *Pediatr. Res.*, 39(4):185A (1996).

Suter et al., "Granulocyte Neutral Proteases and Pseudomonas Elastase as Possible Causes of Airway Damage in Patients with Cystic Fibrosis," *J. Infect. Dis.*, 149(4):523–531 (1984).

Tack et al., "[7] The Third, Fourth, and Fifth Components of Human Complement: Isolation and Biochemical Properties," *Methods in Enzymology: Proteolytic Enzymes, vol. 80*, Lorand, ed., Academic Press, Inc., NY, Title page, publication page, and pp. 64–101 (1981).

Towbin et al., "Electrophoretic transfer of proteins from polyacrylamide gels to nitrocellulose sheets: Procedure and some applications," *Proc. Natl. Acad. Sci. USA*, 76(9):4350–4354 (1979).

Tolins et al., "Modulation of Tubular C–3 Deposition by Ammonia: Quantitation by Antibody Binding," Abstract 39, Meeting of the American Society of Nephrology, New Orleans, Dec. 15–18, 1985, *Kidney Int.*, 29:293 (1986).

Tolins et al., "Hypokalemic Nephropathy in the Rat: Role of Ammonia in Chronic Tubular Injury," *J. Clin. Invest.*, 79(5):1447–1458 (1987).

Wani et al., "Identification, Cloning, and Sequencing of the Immunoglobulin A1 Protease Gene of *Streptococcus pneumoniae*," *Infect. Immun.*, 64(10):3967–3974 (1996).

Wolff et al., "Direct Gene Transfer into Mouse Muscle in Vivo," *Science*, 247(4949):1465–1468 (1990).

Xiang et al., "A Modified Alkaline Lysis Miniprep Protocol Using a Single Microcentrifuge Tube," *BioTechniques*, 17(1):30–32 (1994).

Yother et al., "Transformation of Encapsulated *Streptococcus pneumoniae*," *J. Bacteriol.*, 168(3):1463–1465 (1986).

Yother et al., "Structural Properties and Evolutionary Relationships of PspA, Surface Protein of *Streptococcus pneumoniae*, as Revealed by Sequence Analysis," *J. Bacteriol.*, 174(2):601–609 (1992).

Yother et al., "Novel Surface Attachment Mechanism of the *Streptococcus pneumoniae* Protein PspA," *J. Bacteriol.*, 176(10):2976–2985 (1994).

Zach et al., "Structural and Functional Aberrancies in Neonatal C3," Abstract 1654, Joint Meeting of the American Pediatric Society and the Society for Pediatric Research, Washington, May 2–5, 1988, *Pediatr. Res.*, 23 (4 Part 2):477A (1988).

Zach et al., "Biochemical Abnormalities of the Third Component of Complement in Neonates," *Pediatr. Res.*, 26(2):116–120 (1989).

Zach et al., "Mechanism of Glucocorticoid Stimulation of C3 Synthesis by A549 Type II Cells," Abstract, *J. Clin. Res.*, 38(3):837A (1990).

Zach et al., "Glucocorticoids Enhance the Synthesis of Functionally Active C3 from Type II Cells," Abstract 2168, Ann. Meeting of the American Pediatric Society and the Society for Pediatric Research, Anaheim, May 7–10, 1990, *Pediatr. Res.*, 27 (4 Part 2):364A (1990).

Zach et al., "C3 Gene Expression in Pulmonary Epithelial Cells is Enhanced by Glucocorticoids," Abstract 977, Ann. Meeting of the American Pediatric Society and the Society for Pediatric Research, New Orleans, Apr. 29–May 2, 1991, *Pediatr. Res.*, 29(4 Part 2):165A (1991).

Zach et al., "Effect of Glucocorticoids on C3 Gene Expression by the A549 Human Pulmonary Epithelial Cell Line," *J. Immunol.*, 148(12):3964–3969 (1992).

* cited by examiner

C3 DEGRADING PROTEINASE GENE SEQUENCE (726 bp)(SEQ ID NO:1)

```
1183                                          atgaatgt aaatcagatt
1201 gtacggatta ttcctacttt aaaagctaat aatagaaaat taaatgaaac
1251 attttatatt gaaaccttg gaatgaaggc cttgttagaa gaatcggcct
1301 ttctgtcact aggtgaccaa acgggtcttg aaaagctggt tttagaagaa
1351 gctcccagta tgcgtactcg taaggtagag ggaagaaaaa aactagctag
1401 attgattgtc aaggtggaaa atcccttaga aattgaagga atcttatcta
1451 aaacagattc gattcatcga ttatataaag gtcaaaatgg ctacgctttt
1501 gaaattttct caccagaaga tgatttgatt ttgattcatg cggaagatga
1551 catagcaagt ctagtagaag taggagaaaa gcctgaattt caaacagatt
1601 tggcatcaat ttctttaagt aaatttgaga tttctatgga attacatctc
1651 ccaactgata tcgaaagttt cttggaatca tctgaaattg gggcatccct
1701 tgattttatt ccagctcagg ggcaggattt gactgtggac aatacggtta
1751 cctgggactt atctatgctc aagttcttgg tcaatgaatt agacatagca
1801 agtcttcgcc agaagtttga gtctactgaa tattttattc ctaagtctga
1851 aaaattcttc cttggtaaag atagaaataa tgttgaattg tggtttgaag
1901 aagtatga
```

Fig. 1A

C3 DEGRADING PROTEINASE PROTEIN SEQUENCE (241aa)(SEQ ID NO:2)

```
  1  MNVNQIVRII PTLKANNRKL NETFYIETLG MKALLEESAF LSLGDQTGLE
 51  KLVLEEAPSM RTRKVEGRKK LARLIVKVEN PLEIEGILSK TDSIHRLYKG
101  QNGYAFEIFS PEDDLILIHA EDDIASLVEV GEKPEFQTDL ASISLSKFEI
151  SMELHLPTDI ESFLESSEIG ASLDFIPAQG QDLTVDNTVT WDLSMLKFLV
201  NELDIASLRQ KFESTEYFIP KSEKFFLGKD RNNVELWFEE V*
```

HUMAN COMPLEMENT C3-DEGRADING PROTEIN FROM STREPTOCOCCUS PNEUMONIAE

This patent application claims benefit of Provisional application Ser. No. 60/044,316 filed Apr. 24, 1997.

STATEMENT OF GOVERNMENT SUPPORT

The invention was made with the support of National Institutes of Health grant number R01-AI24162. The U.S. government may have certain rights to the invention.

FIELD OF THE INVENTION

This invention relates to *Streptococcus pneumoniae* and in particular this invention relates to the identification of an *S. pneumoniae* protein that is capable of degrading human complement protein. C3.

BACKGROUND OF THE INVENTION

This application claims the benefit of a provisional application (Ser. No. 60/044,316) filing on Apr. 24, 1997 entitled "Human complement C3-degrading proteinase from *Streptococcus pneumoniae*."

Respiratory infection with the bacterium *Streptococcus pneumoniae* (*S. pneumoniae*) leads to an estimated 500,000 cases of pneumonia and 47,000 deaths annually. Those persons at highest risk of bacteremic pneumococcal infection are infants under two years of age and the elderly. In these populations. *S. pneumoniae* is the leading cause of bacterial pneumonia and meningitis. Moreover, *S. pneumoniae* is the major bacterial cause of ear infections in children of all ages. Both children and the elderly share defects in the synthesis of protective antibodies to pneumococcal capsular polysaccharide after either bacterial colonization, local or systemic infection, or vaccination with purified polysaccharides. *S. pneumoniae* is the leading cause of invasive bacterial respiratory disease in both adults and children with HIV infection and produces hematogenous infection in these patients (Connor et al. *Current Topics in AIDS* 1987;1:185–209 and Janoff et al. *Ann. Intern. Med* 1992;117 (4):314–324).

Individuals who demonstrate the greatest risk for severe infection are not able to make antibodies to the current capsular polysaccharide vaccines. As a result, there are now four conjugate vaccines in clinical trial. Conjugate vaccines consist of pneumococcal capsular polysaccharides coupled to protein carriers or adjuvants in an attempt to boost the antibody response. However, there are other potential problems with conjugate vaccines currently in clinical trials. For example, pneumococcal serotypes that are most prevalent in the United States are different from the serotypes that are most common in places such as Israel. Western Europe, or Scandinavia. Therefore, vaccines that may be useful in one geographic locale may not be useful in another. The potential need to modify currently available capsular polysaccharide vaccines or to develop protein conjugates for capsular vaccines to suit geographic serotype variability entails prohibitive financial and technical complications. Thus, the search for immunogenic, surface-exposed proteins that are conserved worldwide among a variety of virulent serotypes is of prime importance to the prevention of pneumococcal infection and to the formulation of broadly protective pneumococcal vaccines. Moreover, the emergence of penicillin and cephalosporin-resistant pneumococci on a worldwide basis makes the need for effective vaccines even more exigent (Baquero et al. *J. Antimicrob. Chemother.* 1991;28S;31–8).

Several pneumococcal proteins have been proposed for conjugation to pneumococcal capsular polysaccharide or as single immunogens to stimulate immunity against *S. pneumoniae*. Surface proteins that are reported to be involved in adhesion of *S. pneumoniae* to epithelial cells of the respiratory tract include PsaA, PspC/CBP112, and IgA1 proteinase (Sampson et al. *Infect. Immun.* 1994;62:319–324, McDaniel et al., *Microb. Pathogen.* 1992; 13:261–9, and Wani, et al. *Infect. Immun.* 1996; 64;3967–3974). Antibodies to these adhesins could inhibit binding of pneumococci to respiratory epithelial cells and thereby reduce colonization. Other cytosolic pneumococcal proteins such as pneumolysin, autolysin, neuraminidase, or hyaluronidase are proposed as vaccine antigens because antibodies could potentially block the toxic effects of these proteins in patients infected with *S. pneumoniae*. However, these proteins are typically not located on the surface of *S. pneumoniae*, rather they are secreted or released from the bacterium as the cells lyse and die (Lee et al. *Vaccine* 1994; 12:875–8 and Berry et al. *Infect. Immun.* 1994; 62:1101–1108). While use of these cytosolic proteins as immunogens might ameliorate late consequences of *S. pneumoniae* infection, antibodies to these proteins would neither promote pneumococcal death nor prevent initial or subsequent pneumococcal colonization.

A prototypic surface protein that is being tested as a pneumococcal vaccine is the pneumococcal surface protein A (PspA). PspA is a heterogeneous protein of about 70–140 kDa. The PspA structure includes an alpha helix at the amino terminus, followed by a proline-rich sequence, and terminates in a series of 11 choline-binding repeats at the carboxy-terminus. Although much information regarding its structure is available, PspA is not structurally conserved among a variety of pneumococcal serotypes, and its function is entirely unknown (Yother et al. *J. Bacteriol.* 1992:174:601–9 and Yother *J. Bacteriol.* 1994;176:2976–2985). Studies have confirmed the immunogenicity of PspA in animals (McDaniel et al. *Microb. Pathogen.* 1994; 17;323–337). Despite the immunogenicity of PspA, the heterogeneity of PspA, its existence in four structural groups (or clades), and its uncharacterized function complicate its ability to be used as a vaccine antigen.

In patients who cannot make protective antibodies to the type-specific polysaccharide capsule, the third component of complement, C3, and the associated proteins of the alternative complement pathway constitute the first line of host defense against *S. pneumoniae* infection. Because complement proteins cannot penetrate the rigid cell wall of *S. pneumoniae*, deposition of opsonic C3b on the pneumococcal surface is the principal mediator of pneumococcal clearance. Interactions of pneumococci with plasma C3 are known to occur during pneumococcal bacteremia, when the covalent binding of C3b, the opsonically active fragment of C3, initiates phagocytic recognition and ingestion (Johnston et al. *J. Exp. Med* 1969:129:1275–1290, Jasin H E, *J. Immunol.* 1972; 109:26–31 and Hostetter et al. *J. Infect. Dis.* 1984; 150:653–61). C3b deposits on the pneumococcal capsule, as well as on the cell wall. This method for controlling *S. pneumoniae* infection is fairly inefficient. Methods for augmenting *S. pneumoniae* opsonization could improve the disease course induced by this organism. There currently exists a strong need for methods and therapies to limit *S. pneumoniae* infection.

SUMMARY OF THE INVENTION

This invention relates to the identification and use of a family of human complement C3-degrading proteinases expressed by *S. pneumoniae*. The protein has a molecular weight of about 24 kD to about 34 kD as determined on a 10% SDS polyacrylamide gel. The invention includes a number of proteins isolatable from different C3-degrading strains of *S. pneumoniae*.

In one aspect of the invention, the invention relates to an isolated protein comprising at least an 80% sequence identity of SEQ ID NO:2 and capable of degrading human complement protein C3. In a preferred embodiment, the protein is isolated from *S. pneumoniae* or alternatively the protein is a recombinant protein. Preferably the protein binds human complement protein C3. In a preferred embodiment, the protein has a molecular weight as determined on a 10% polyacrylamide gel of between about 24 kDa to about 34 kDa. A preferred protein of this invention is an isolated protein including SEQ ID NO:2.

The invention also relates to peptides from the C3-degarding proteinase of this invention and preferably peptides of at least 15 sequential amino acids from an isolated protein comprising at least an 80% sequence identity of SEQ ID NO:2 and capable of degrading human complement protein C3 and more preferably peptides of at least 15 sequential amino acids from SEQ ID NO:2.

The protein of claim 9, wherein the protein is a recombinant protein. In another aspect of this invention, the invention relates to a peptide of at least 15 sequential amino acids from SEQ ID NO:2.

The protein of this invention can comprise SEQ ID NO:2, and preferably has a molecular weight as determined on a 10% polyacrylamide gel of between about 24 kDa to about 34 kDa. Also preferably the protein degrades human complement protein C3. Preferred protein or polypeptides of this invention include a protein comprising amino acids 1–50 of SEQ ID NO:2 and a nucleic acid fragment comprising nucleic acids 1246 to 1863 of FIG. 1A.

In another aspect of the invention the invention relates to a protein that degrades human complement protein C3 and wherein nucleic acid encoding the protein hybridizes to SEQ ID NO:1 under hybridization conditions of 6×SSC, 5×Denhardt, 0.5% SDS, and 100 µg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes.

The invention also relates to an immune-system stimulating composition comprising an effective amount of an immune system-stimulating peptide or polypeptide comprising at least 15 amino acids from a protein comprising at least an 80% sequence identity with SEQ ID NO:2 and capable of degrading human complement protein C3.

Preferably the protein is isolatable from *S. pneumoniae*. In one embodiment, the immune system stimulating composition further comprises at least one other immune stimulating peptide, polypeptide or protein from *S. pneumoniae*.

The invention further relates to an antibody capable of specifically binding to a protein comprising at least a 80% sequence identity with SEQ ID NO:2 and capable of degrading human complement protein C3. In one embodiment, the antibody is a monoclonal antibody an din an other embodiment, the antibody is a polyclonal antibody. In another embodiment the antibody is an antibody fragment. The antibody or antibody fragments can be obtained from a mouse, a rat, human or a rabbit.

The invention also relates to a nucleic acid fragment capable of hybridizing to SEQ ID NO:1 under hybridization conditions of 6×SSC, 5×Denhardt, 0.5% SDS, and 100 µg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes. In one embodiment the nucleic acid fragment is isolated from an *S. pneumoniae* genome and in another embodiment, the nucleic acid fragment encodes at least a portion of a protein. In one embodiment, the protein degrades human complement C3 and in another embodiment, the nucleic acid fragment encodes a protein that does not degrade human complement C3.

In another embodiment, the nucleic acid fragment is in a nucleic acid vector and the vector can be an expression vector capable of producing at least a portion of a protein. Cells containing the nucleic acid fragment are also contemplated in this invention. In one embodiment, the cell is a bacterium or a eukaryotic cell.

The invention further relates to an isolated nucleic acid fragment comprising the nucleic acid sequence gctcccagtat-gcgtactcgtaaggtagagggaagaaaaaaactagctag. SEQ ID NO:9.

In another aspect of this invention, the invention relates to a method for producing an immune response to *S. pneumoniae* in an animal including the steps of: administering a composition comprising a therapeutically effective amount of at least a portion of a protein to an animal, wherein nucleic acid encoding the protein hybridizes to SEQ ID NO:1 under hybridization conditions of 6×SSC, 5×Denhardt, 0.5% SDS, and 100 µg/ml fragmented and denatured salmon sperm DNA, hybridized overnight at 65° C. and washed in 2×SSC, 0.1% SDS one time at room temperature for about 10 minutes followed by one time at 65° C. for about 15 minutes followed by at least one wash in 0.2×SSC, 0.1% SDS at room temperature for at least 3–5 minutes; and obtaining an immune response to the protein. In one embodiment the immune response is a B cell response and in another embodiment, the immune response is a T cell response. In a preferred embodiment, the composition is a vaccine composition. Preferably the at least a portion of the protein is at least 15 amino acids in length and also preferably the composition further comprises at least one other protein from *S. pneumoniae*. In one embodiment, the protein comprises at least 15 amino acids of SEQ ID NO:2.

In a further embodiment, the invention relates to a bacteria comprising an insertional mutation, wherein the insertion mutation is in a gene encoding a protein capable of degrading human complement C3. In one embodiment, the bacteria comprises an insertional duplication mutation.

The invention further relates to an isolated protein of about 24 kDa to about 34 kDa from *Streptococcus pneumoniae* that is capable of binding to and degrading human complement C3 and to a method for inhibiting *Streptococcus pneumoniae*-mediated C3 degradation comprising the step of: contacting a *Streptococcus pneumonia* bacterium with antibody capable of binding to a protein with at least 80% amino acid sequence identity to SEQ ID NO:2. The invention further relates to an isolated nucleic acid fragment comprising the nucleic acid sequence of SEQ ID NO:1 and to an RNA fragment transcribed by a double-stranded DNA sequence comprising SEQ ID NO:1.

BRIEF DESCRIPTION OF THE FIGURES

FIG. 1A provides a gene sequence and FIG. 1B provides an amino acid sequence of a C3 degrading proteinase of this invention.

DETAILED DESCRIPTION OF THE PREFERRED EMBODIMENTS

Figure 2:
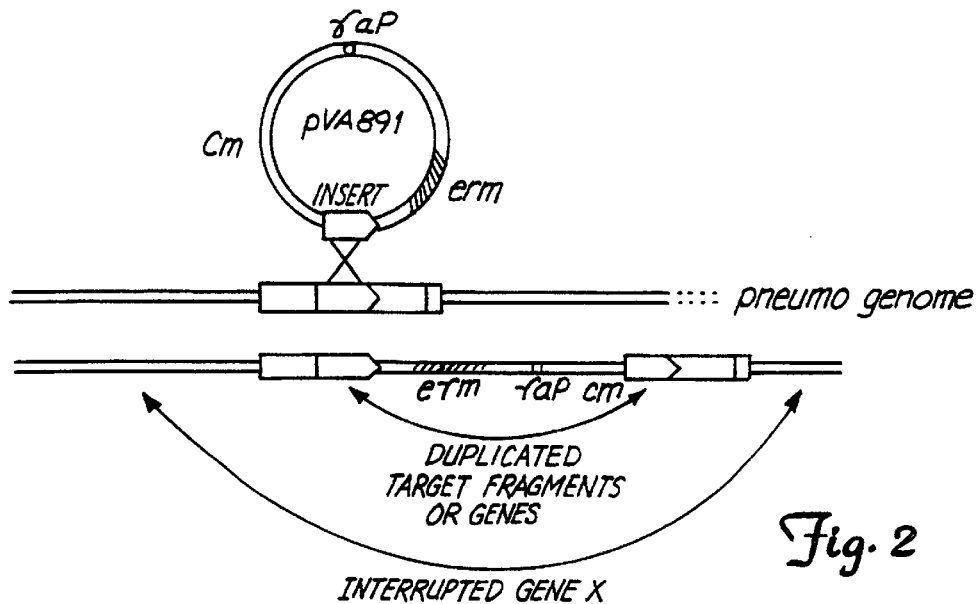
FIG. 2 is a diagram of an insertion duplication mutant according to this invention.

The present invention relates to the identification and isolation of a C3 degrading proteinase with a molecular weight of about 29 kDa (±5 kDa) on a 10% SDS-PAGE gel (with a predicted size of about 27.5 kDa based on SEQ ID NO:1) and nucleic acid encoding the C3 degrading proteinase. The protein was originally identified by electrophoresis of pneumococcal lysates on SDS-PAGE gels impregnated with C3. It has been observed that exponentially growing cultures of pneumococci from several serotypes were able to first degrade the β-chain then degrade the α chain of C3 without producing defined C3 cleavage fragments (Angel, et al. *J. Infect. Dis.* 170:600–608, 1994). This pattern of degradation without cleavage differs substantially from other microbial products such as the elastase moiety of *Pseudomonas aeruginosa* and the cysteine proteinase of *Entamoeba histolytica*. The gene sequence (SEQ ID NO:1) encoding a C3 degrading protein according to this invention is provided in FIG. 1A and the amino acid sequence (SEQ ID NO:2) of the protein is provided in FIG. 1B.

The term "degrade" is used herein to refer to enzymes that are capable of cleaving proteins into amino acids, peptides and/or polypeptide fragments. The proteins of this invention degrade C3 without producing specific cleavage fragments as observed on a polyacrylamide gel.

A C3-degrading proteinase of about 29 kDa was isolated from a library of insertionally interrupted pneumococcal genes by identifying those clones that had increased C3 degrading activity as compared to wild type *S. pneumoniae*. There is at least some preference of the C3-degrading proteinases of this invention for C3 in that, for example, the C3-degrading proteinase does not degrade other proteins, such as albumin, to a large extent. Exemplary methods for performing insertion duplication mutagenesis and for the identification of clones with elevated C3 degrading activity is provided in Example 1.

A gene encoding a C3-degrading proteinase is contained within a region that includes four open reading frames and interruption of the third open reading frame by homologous recombination severely impaired C3 degradation. ORF3 includes about 726 nucleotides and the sequence of the translated protein shares no substantial homology with proteins registered in either the GenBank or SwissProt databases.

The full length gene encoding a C3-degrading proteinase of this invention was inserted into a gene expression vector for expression in *E. coli*. Recombinant C3-degrading proteinase was isolated as described in the examples. Those of ordinary skill in the art recognize that, given a particular gene sequence such as that provided in FIG. 1, there are a variety of expression vectors that could be used to express the gene. Further, there are a variety of methods known in the art that could be used to produce and isolate the recombinant protein of this invention and those of ordinary skill in the art also recognize that the C3 degrading assay of this invention will determine whether or not a particular expression system, in addition to those expression systems provided in the examples, is functioning, without requiring undue experimentation. A variety of molecular and immunological techniques can be found in basic technique texts such as those of Sambrook et al. (*Molecular Cloning, A Laboratory Manual*, 1989 Cold Spring Harbor Laboratory Press, Cold Spring Harbor, N.Y.) and Harlow et al. (*Antibodies; A Laboratory Manual*, Cold Spring Harbor, N.Y.; Cold Spring harbor Laboratory Press, 1988).

The gene encoding the C3 degrading protein of this invention was identified using a plasmid library made with pneumococcal genomic DNA fragments from strain CP1200. Although there are a variety of methods known for obtaining a plasmid library; in a preferred strategy, a plasmid library was constructed with Sau 3A digested pneumococcal genomic DNA fragments (0.5–4.0 kb) from pneumococcal strain CP 1200 (obtained from D. A. Morrison, University of Illinois, Champagne-Urbana, Ill. and described in Havarstein L F, et al. *Proc. Natl. Acad. Sci.* (USA) 1995;92:11140–11144) and inserted into the Bam HI site of the integrative shuttle vector pVA 891 (erm$^r$, cm$^r$; has origin of replication for *E. coli*). This library was transformed into an *E. coli* DHLα MCR strain by electroporation. A total of 14000 *E. coli* transformants were obtained by electroporation. Plasmid extractions of some randomly selected *E. coli* transformants revealed that all of them contained recombinant plasmids.

Plasmid library DNA was extracted from the *E. coli* transformants and was used to transform the CP 1200 parent pneumococcal strain using insertional mutatgenesis homologous recombination.

The pneumococcal strain CP 1200 cells were made competent using a pH shift with HCl procedure in CTM medium. The competent cells were frozen at −70° C. in small aliquots until needed. Eight thousand pneumococcal transformants were produced using these methods.

Individual pneumococcal transformants were screened by ELISA for their altered phenotypic character based on their ability to degrade C3. Bacterial cultures were incubated with C3 (0.83 μg of C3/ml of culture) for about 2 hrs to about 4 hrs and the amount of undegraded C3 left in the samples was detected by enzyme linked immunoadsorbent assays (ELISA) using HRP-conjugated goat polyclonal antibody specific to human complement C3. The assay was standardized so that wells containing undegraded C3 had an O.D. 490=~1.0. Wells containing degraded C3 had a reduced optical density resulting from their reduced ability to bind anti-C3 antibodies. The optical densities of the mutant and parent strains were compared to that of negative controls. The negative controls were culture medium containing different concentrations of C3. The percent of C3 degrading activity was determined as a ratio of optical density of sample to control. Four mutants (SN3, SN4, SN5 and SN6) were identified with elevated C3 degrading activity (about 2–2.2 fold higher activity) as compared with the activity of the about 29 kDa C3-degrading protein from parent strain CP1200. This finding was confirmed by Western Blot analysis.

Total DNA from mutants SN3, SN4, SN5 and SN6 was isolated and used for electroporation into *E. coli* DH5α MCR. Low excision rates of plasmid DNA from integrated plasmids within the pneumonocci genome can produce small amounts of free plasmid DNA and this DNA can be recovered when the DNA is transformed into *E. coli*. This allows further characterization of the plasmid. Retransformation of the plasmid back into pneumococcus verifies the phenotype of the original mutant.

Protein samples from the native C3-degrading protein and from mutants SN3, SN4, SN5, SN6 were incubated with C3 and separated on a 7.5% SDS-PAGE gel under reducing conditions. C3 degrading activity was assessed using western blot analysis employing HRP-conjugated antibody to C3. Mutant SN4 and mutant SN4-4G were used in further experiments. Mutant SN4-4G was identified after CP 1200 was retransformed with the recombinant plasmid pLSN4a rescued from SN4. Both mutant SN4 and mutant SN4-4G almost completely degraded C3 after a 4 hr incubation. While the native C3 degrading protein degraded C3, after a 4 hr incubation, C3 degradation was incomplete as compared with a comparable incubation using mutants SN4 and mutant SN4-4G.

The plasmid encoding the protein from mutant SN4 was chosen for further investigation. Plasmid pLSN4a (encoding mutant SN4) was used to retransform the wild type CP 1200 strain. This resulted in 48 pneumococcal mutants with elevated C3 degrading activity. Digestion with restriction endonuclease Hind III demonstrated that plasmid pLSN4a was about ~7.8 kb and included an insert that was about ~2.3 kb.

Plasmid pLSN4a was used as a hybridization probe in southern hybridization experiments to verify the presence of the insert in chromosomal DNA samples from the pneumococcal mutants. The results confirmed that the vector with insert (pLSN4a) and also the origin of the inserts in the mutants SN3 and SN4 were integrated in the chromosomal DNA. Both mutants SN3 and SN4 consisted of two hybridizing junction fragments of sizes about ~2.2 kb and about ~5.8 kb. These fragments were also present in their parent strain CP1200. There were two other hybridizing fragments at about ~4.2 kb and about ~3.5 kb and these two fragments together gave a total of about ~7.8 kb (pLSN4 a is ~7.8 kb). These two bands were also present in the vector with insert sample. Both insert and vector included EcoR 1 sites and represent the recombinant plasmid. Analysis indicated that a gene duplication had occurred in the SN4 mutant strain; therefore, the improved C3-degradation activity could be attributed to increased C3-degrading protein in the SN4 mutants.

The sequence of about 1 kb of the 2338 bp insert was determined using whole pLSN4a plasmid as a template. The remaining sequence (about ~1338 bp) with just insert (PCR product) as a template, was sequenced by ICBR, University of Florida. Both complementary strands were sequenced. The results indicated that there were four open reading frames with the relative locations provided in the schematic below:

No significant homology was found between the derived amino acid sequence of the above ORFs and protein sequences from the protein databases tested. The ORF3 nucleic acid sequence encoding a C3 degrading proteinase of this invention is provided in FIG. 1A and is designated SEQ ID NO:1. The amino acid sequence of this C3 degrading proteinase is provided in FIG. 1B and is designated SEQ ID NO:2.

Out of four opening reading frames (three full and one partial) in the insert, the ORF3 was chosen for further examination because it contained the largest insert. A 620 bp internal portion (from nucleic acid 1246 to nucleic acid 1863 of FIG. 1A) of ORF3 (PCR product) region was ligated into the Hind III site of plasmid pVA 891 and the construct was transformed into CP 1200 competent cells to knock out the proteinase activity. The transformants were tested for their ability to degrade C3 after separation on SDS-page gels using western blot analysis. The ORF3 disruption mutant had poor activity in comparison with its parent strain CP 1200.

The entire ORF3 gene (PCR product) was cloned into Nde I and Bam H I sites of pet-28b(+). The vector positions a His-Tag at the N-terminus of the protein. The plasmid construct was transformed into an E. coli (DHLα MCR) strain for stabilization before it was transformed into an E. coli (BL 21 DE3) protease deficient strain for protein expression.

The BL 21 DE3 strain that included the construct (pet 28b(+) with ORF3) was induced for ORF3 protein expression. Total cell protein extracts of the induced and uninduced cultures were tested for C3 degrading activity. The expressed His-tagged ORF3 protein was about ~29 kDa (±5 kDa) on 10% SDS-PAGE gels in the induced samples from the insoluble protein fraction.

Solubilization of the ORF 3 protein from induced BL21 DE3 cultures was performed by treating the sample with: a) TES (50 mM, 1 mM, 1M); b) 6 mM G-HCl+1 mM DTT; c) 6 mM G-HCl+1 mM DTT+1% Tween 20; and d) 6 mM G-HCl+1 mM DTT+1% Triton X-100. Both treatments "c" and "d" resulted in soluble protein. Treatment "c" was used to produce solubilized recombinant C3 degrading protein that was used for further protein studies.

Guanidine-HCl and DTT were removed from the expressed His-Tagged ORF3 protein samples by dialysis. The protein was subjected to Nickel column purification and the eluted His-Tagged protein was visualized on a 10% SDS-PAGE gel.

The isolated protein encoded by ORF 3 was incubated with human complement C3 for 4 hrs at 37° C. in the presence of PBS. Control samples without the protein samples were used as negative controls for comparative purposes. The samples were run on SDS-PAGE gel under reducing conditions and analyzed for the structure of C3 by Western Blot assay using polyclonal antibodies to human complement C3. The results indicated that the samples contained a protein encoded by the ORF 3 region and that the protein degraded human C3 protein. Both α and β chains of C3 molecules were susceptible to degradation. In these experiments while the α chain was almost completely degraded, the β chain was also degraded, but to a somewhat lesser extent.

The C3 degrading proteins of this invention were designated CppA proteinases and the genes of this invention are designated cppA. The proteins of this invention have an apparent molecular weight on a 10% SDS-polyacrylamide gel of about 29 kDa (±5 kDa) and preferably has a molecular weight of about 24 kDa to about 34 kDa. As described above, Example 5 indicates that the proteinase is conserved throughout S. pneumoniae strains. However, those of ordinary skill in the art will recognize that some variability in amino acid sequence is expected and that this variability should not detract from the scope of this invention. For example, conserved mutations do not detract from this invention nor do variations in amino acid sequence identity of less than about 80% amino acid sequence identity and preferably less than about 90% amino acid sequence identity where the protein is capable of degrading human complement protein C3, and particularly where the protein is isolated or originally obtained from an *S. pneumoniae* bacterium.

Some nucleic acid sequence variability is expected among the strains as is some amino acid variability. Conserved amino acid substitutions are known in the art and include, for example, amino acid substitutions using other members from the same class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to affect apparent molecular weight as determined by polyacrylamide gel electrophoresis or isoelectric point. Particularly preferred conservative substitutions include, but are not limited to, Lys for Arg and vice verse to maintain a positive charge; Glu for Asp and vice versa to maintain a negative charge; Ser for Thr so that a free —OH is maintained; and Gln for Asn to maintain a free $NH_2$. A preferred protein of this invention includes a protein with the amino acid sequence of SEQ ID NO:2. Other proteins include those degrading human complement protein C3 and having nucleic acid encoding the protein that hybridizes to SEQ ID NO:1 under hybridization conditions of 6×SSC, 5×Denhardt, 0.5% SDS, and 100 μg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes are also contemplated in this invention. Polypeptides or peptide fragments of the protein can also be used and a preferred protein of this invention comprises amino acids 1–50 of SEQ ID NO:2.

The proteins of this invention can be isolated or prepared as recombinant proteins. That is, nucleic acid encoding the protein, or a portion of the protein. can be incorporated into an expression vector or incorporated into a chromosome of a cell to express the protein in the cell. The protein can be purified from a bacterium or another cell, preferably a eukaryotic cell and more preferably an animal cell. Alternatively, the protein can be isolated from a cell expressing the protein, such as a *S. pneumoniae* cell. Peptides of the CppA proteinase are also considered in this invention. The peptides are preferably at least 15 amino acids in length and preferred peptides are peptides with at least 15 sequential amino acids from SEQ ID NO:2. Another preferred protein fragment includes amino acids 1–50 of SEQ ID NO:2.

Nucleic acid encoding CppA proteinase is also part of this invention. SEQ ID NO:1 is a preferred nucleic acid fragment encoding a CppA proteinase. Those of ordinary skill in the art will recognize that some substitution will not alter the CppA proteinase sequence to an extent that the character or nature of the CppA proteinase is substantially altered. For example, nucleic acid with an identity of at least 80% to SEQ ID NO:1 is contemplated in this invention. A method for determining whether a particular nucleic acid sequence falls within the scope of this invention is to consider whether or not a particular nucleic acid sequence encodes a C3-degrading proteinase and has a nucleic acid identity of at least 80% as compared with SEQ ID NO:1. Other nucleic acid sequences encoding the CppA proteinase includes nucleic acid encoding CppA where the CppA has the same sequence or at least a 90% sequence identity with SEQ ID NO:2 but which includes degeneracy with respect to the nucleic acid sequence. A degenerate codon means that a different three letter codon is used to specify the same amino acid. For example, it is well known in the art that the following RNA codons (and therefore, the corresponding DNA codons, with a T substituted for a U) can be used interchangeably to code for each specific amino acid:

| | |
|---|---|
| Phenylalanine (Phe or F) | UUU or UUC |
| Leucine (Leu or L) | UUA, UUG, CUU, CUC, CUA or CUG |
| Isoleucine (Ile or I) | AUU, AUC or AUA |
| Methionine (Met or M) | AUG |
| Valine (Val or V) | GUU, GUC, GUA, GUG |
| Serine (Ser or S) | UCU, UCC, UCA, UCG, AGU, AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU, CGC, CGA, CGG, AGA, AGC |
| Glycine (Gly or G) | GGU or GGC or GGA or GGG |
| Termination codon | UAA, UAG or UGA |

Further, a particular DNA sequence can be modified to employ the codons preferred for a particular cell type. For example, the preferred codon usage for *E. coli* is known, as are preferred codons for animals and humans. These changes are known to those of ordinary skill in the art and therefore these gene sequences are considered part of this invention. Other nucleic acid sequences include nucleic acid fragments of at least 30 nucleic acids in length from SEQ ID NO:1 or other nucleic acid fragments of at least 30 nucleic acids in length where these fragments hybridize to SEQ ID NO:1 under hybridization conditions of 6×SSC, 5×Denhardt, 0.5% SDS, and 100 μg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes.

The nucleic acid fragments of this invention can encode all, none (i.e., fragments that cannot be transcribed, fragments that include regulatory portions of the gene, or the like) or a portion of SEQ ID NO:2 and preferably containing a contiguous nucleic acid fragment that encodes at least nine amino acids from SEQ ID NO:2. Because nucleic acid fragments encoding a portion of the CppA proteinase are contemplated in this invention, it will be understood that not all of the nucleic acid fragments will encode a protein, polypeptide or peptide with C3 degrading activity. Further, the nucleic acid of this invention can be mutated to remove or otherwise inactivate the C3 degrading activity of this protein. Therefore, fragments without C3 degrading activity that meet the hybridization requirements described above are also contemplated. Methods for mutating or otherwise altering nucleic acid sequences are well described in the art and the production of an immunogenic, but enzymatically inactive protein can be tested for therapeutic utility. Preferred nucleic acid fragments include gct ccc agt atg (claim 34).

The nucleic acid fragments of this invention can be incorporated into nucleic acid vectors or stably incorporated into host genomes to produce recombinant protein including recombinant chimeric protein. A variety of nucleic acid vectors are known in the art and include a number of commercially available expression plasmids or viral vectors. The use of these vectors is well within the scope of what is ordinary skill in the art. Exemplary vectors are employed in the examples, but should not be construed as limiting on the scope of this invention.

This invention also relates to antibody capable of binding specifically to a protein of about 29 kDa, and preferably a protein of about 24 kDa to about 34 kDa, from S. pneumoniae and preferably where the protein is capable of degrading human complement C3. Polyclonal antibody can be prepared to a portion of the protein or to all of the protein. Similarly, monoclonal antibodies can be prepared to all or to a peptide fragment of the about 29 kDa C3 degrading protein of this invention. Methods for preparing antibodies to protein are well known and well described, for example, by Harlow, et al. (supra). In a preferred example, the antibodies can be human derived, rat derived, mouse derived or rabbit derived. Protein-binding antibody fragments and chimeric fragments are also known and are within the scope of this invention.

The invention also relates to the use of immune stimulating compositions. The term "immune stimulating" or "immune system stimulating" refers to protein or peptide compositions according to this invention that activates at least one cell type of the immune system. Preferred activated cells of the immune system include phagocytic cells such as macrophages, as well as T cells and B cells. Immune stimulating compositions comprising the peptides, polypeptides or proteins of this invention can be used to produce antibody in an animal such as a rat, mouse, rabbit, a human or an animal model for studying S. pneumoniae infection. Preferred immune stimulating compositions include an immune stimulating amount of at least a peptide including at least 15 amino acids from the CppA proteinase. The immune stimulating composition can further include other proteins in a pharmaceutically acceptable buffer, such as PBS or another buffer recognized in the art as suitable and safe for introduction of proteins into a host to stimulate the immune system. The immune stimulating compositions can also include other immune system stimulating proteins such as adjuvants or immune stimulating proteins or peptide fragments from S. pneumoniae or other organisms. For example, a cocktail of peptide fragments may be most useful for controlling S. pneumoniae infection. Preferably one or more fragments of the proteins of this invention are used in a vaccine preparation to protect against or limit S. pneumoniae colonization or the pathogenic consequences of S. pneumoniae colonization.

This invention also relates to a method for inhibiting Streptococcus pneumoniae-mediated C3 degradation comprising contacting a Streptococcus pneumonia bacterium with a protein, such as an antibody or another protein that is capable of binding to an isolated protein of about 24 kDa to about 34 kDa from Streptococcus pneumoniae. The protein capable of binding to an isolated protein of about 24 kDa to about 34 kDa can be an antibody or a fragment thereof or the protein can be a chimeric protein that includes the antibody binding domain, such as a variable domain, from antibody that is capable of specifically recognizing an isolated protein of about 24 kDa to about 34 kDa from Streptococcus pneumoniae having C3 degrading activity.

The isolated S. pneumoniae protein of this invention can be isolated and purified and the isolated protein or immunogenic fragments thereof can be used to produce antibody. Peptide fragments or polypeptide fragments of the protein without C3 degrading ability can be tested for their ability to limit the effects of S. pneumoniae infection. Similarly, the protein of this invention can be modified, such as through mutation to interrupt or inactivate the C3 degrading capacity of the protein. Isolated protein can be used in assays to detect antibody to S. pneumoniae or as part of a vaccine or a multi-valent or multiple protein or peptide-containing vaccine for S. pneumoniae therapy.

It is further contemplated that the proteins of this invention can be surface expressed on vertebrate cells and used to degrade C3, for example, where complement deposition (or activation) becomes a problem, such as in xenotransplantation or in complement-mediated glomerulonephritis. For example, the recombinant protein, or a portion thereof, can be incorporated into xenotransplant cells and expressed as a surface protein or as a secreted protein to prevent or minimize complement deposition (and/or complement-mediated inflammation).

All references and publications cited herein are expressly incorporated by reference into this disclosure. There are a variety of alternative techniques and procedures available to those of skill in the art which would similarly permit one to successfully perform the intended invention in view of the present disclosure. It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

EXAMPLE 1

Generation of Insertional Duplication Mutants and Recovery of Recombinant Plasmids from Selected Mutants In a preferred example, insertion-duplication mutagenesis was used to isolate a gene encoding the C3 degrading proteinase from Streptococcus pneumoniae of this invention. A plasmid library was created with 0.5–4.0 kb chromosomal fragments of pneumococcal strain CP 1200 (derivative of RX1; Morrison, D. A., el al. J. Bacteriol., 156:281–290,1983) originally obtained from Dr. Morrsion's lab, University of Illinois at Chicago and inserted into the Bam HI shuttle vector pVA 891 (erm$^r$, cm$^r$ Macrina, F. L. et. al. Gene 25:145–150, 1983, obtained from Dr. Marcina (Virginia Commonwealth University, Richmond, Va.). pVA891 has resistance markers for erythromycin (erm) and chloramphenicol (cm). The vector has an origin of replication for E. coli, but the origin is non-replicative in Streptococci. Recombinant plasmid can survive when it integrates into the pneumococcal chromosomal DNA by homologous recombination.

E. coli DH5 α MCR competent cells were made according to the procedure given in the Bio-Rad Laboratories manual (Richmond, Calif.) and the library was transformed into the competent cells with Bio-Rad Gene Pulser apparatus (Bio-Rad Laboratories, Richmond, Calif.) by electroporation.

E. coli cells were maintained as freezer stocks in small aliquots at −80° C., in LB broth in the presence of 10% glycerol. The cells were grown either in LB or TB broth or on LB agar plates containing appropriate antibiotics (erythromycin 200 μg/ml or chloramphenicol 15 or 30 μg/ml or kanamycin 30 μg/ml).

Electroporation was conducted in 0.1 cm cuvette at 1–2 kV/cm voltages and a capacitance of 200 Ω. Transformants were selected on LB medium containing either chloramphenicol (cm, 30 μg/ml) or erythromycin (erm, 300 μg/ml) or combination of erm and cm (200 μg/ml+15 μg/ml).

A total of 14000 *E. coli* transformants were obtained from the library. Plasmid extractions and restriction analysis of randomly selected *E. coli* transformants revealed the presence of recombinant plasmids.

Plasmids or recombinant plasmids were extracted from *E. coli* strains by polyethylene glycol precipitation procedure (Kreig. P. and Melton. D., in *Promega Protocols and Applications* p. 106, 1985–86) or a modified alkaline lysis miniprep protocol (Xiang. C., et al., *Biotechniques*. 17:30–32, 1994) a modified alkaline extraction procedure (Bimboim H C and J Doly., *Nucl. Acids Res.* 7:1513–1523, 1979), or CsCl-ethidium bromide gradient method or Qiagen kit (Plasmid midi kit., Chartsworth, Calif.). Solutions containing DNA were cleaned directly from agarose gels by GeneClean II kit (BIO 101, La Jolla, Calif.) or Qiagen kit (DNA extraction from gels., Chartsorth, Calif.). DNA was cleaned by Wizard DNA clean up kit (Promega Corp., Madison, Wis.). Amplified gene products were also cleaned by Wizard PCR clean up kit (Promega Corp., Madison, Wis.).

The plasmids were transformed into Pneumococcal cells. The pneumococcal strains were always maintained as freezer stocks in small aliquots at −80° C., in THB in the presence of 10% glycerol. Pneumococcal cells were grown without shaking in CAT (Morrison, D. A., et al., 1983, supra) or THB medium (broth or agar). For transformation experiments, either complete transformation (CTM) broth (Morrison, D. A., et al., 1983) or THB+0.5% Yeast broth (Yother Janet., et al. *J. Bacteriol.* 168:1463–1465, 1986) and for ELISA experiments, SMP, a synthetic medium (see Table 1) were used. Erythromycin (0.05 μg/ml) was employed as a selective antibiotic marker for pneumococcal mutants.

TABLE 1

SMP - a synthetic medium

SMP solution #1 (final volume 2 liters):

NaCl 10.0 g; NH$_4$Cl 4.0 g; KCl 0.8 g; Na$_2$HPO$_4$ 0.24 g; MgSO$_4$ 0.048 g; CaCl$_2$ 0.020 g; FeSO$_4$.7H$_2$O 0.00011 g; Tribase 9.68 g add d.H$_2$O up to 1 liter pH to 7.55 and then add the following amino acids:
L-Arginine 400 mg; L-Asparagine 20 mg (monohydrate 22.8 mg):
Glycine 240 mg; L-Histidine 300 mg;
L-Isoleucine 13.10 mg; L-Leucine 13.10 mg; L-Lysine 840 mg;
L-methionine 360 mg; (low-methi. 2.6 mg): L-valine 11.70 mg; Uracil 2 mg. Make it up to a final volume of 2 liters.
SMP solution 2 (vitamins):

Biotin 0.075 mg; Choline 25 mg; Nictinamide 3.0 mg; ca pantothenate 12.0 mg; Pyridoxal HCl 3.0 mg; Riboflavin 1.5 mg; Thiamine 3.0 mg; L-Cysteine HCl 0.5 g; L-Glutamine 0.1 g; Na Pyruvate 4.0 g; add water and then make up to 50 ml.
Reconstituting SMP:

| Start with: | ml |
|---|---|
| Solution #1 | 100 |
| Add: | |
| Solution #2 | 1 |
| Solution #3(25% Glucose) | 1.6 |
| Solution #4(4% BSA) | 2 |

Pneumococcal strain CP 1200 cells were made competent by "competence induction by pH shift" (procedure obtained from Dr. Morrison's lab, Univ. of Illinois at Chicago, Ill.) in CTM medium and the competent cells were frozen at −70° C. in small aliquots until required. In this procedure, to 125 ml of CTM added 1.20 ml of 1M HCl (final concentration 9 mM) and 4 ml of 0.2 O.D. (550 nm) of frozen pneumococcal stock cells. This culture was incubated at 37° C. and O.D. readings of the culture were taken at 20 minute intervals beginning after 3 hrs of incubation. When the culture reached an O.D. of 0.156 (550 nm), 1.2 ml of 1N NaOH was added at 37° C. After mixing the culture gently, 1 ml of culture was removed as a '0' time point sample, mixed with 100 μl of glycerol and kept on a prechilled metal block. Similarly, ten ml samples were drawn at each time point of 13, 17, 21 and 25 min and each sample was added directly to prechilled 1 ml of glycerol. Each time point sample was frozen in small aliquots at −70° C. Competence was tested for each time point sample by adding 1 μl of DNA (about 250 ng) to 100 μl of cells and incubating at 37° C. for 25 min for transformation. The transformation culture was diluted and plated on selective medium (erythromycin 0.05 μg/ml). The time point sample that showed the highest transformation efficiency was used for future transformation experiments. Transformation of the extracted recombinant plasmid library from *E. coli* transformants into pneumococcal strain CP1200 yielded about 8,000 pneumococcal transformants indicating that the plasmid was inserted into the CP1200 chromosome via homologous recombination.

Extraction of pneumococcal chromosomal DNA was performed by a slight modification of the method used in the laboratory of Dr. Donald A. Morrison, University of Illinois at Chicago. Pneumococcal cells were grown in THB to an O.D. at 550 nm from 0.3–0.4, then rapidly chilled on ice and 0.5M EDTA was added to a final concentration of 10 mM, the cells were spun at 10,000 g for 10 minutes at 4° C., and the pellets were resuspended in 1:10 volume of cold STE (50 mM Tris-HCl (pH 8.0), 10 mM EDTA (pH 8.0), and 0.1M NaCl). After a second centrifugation, cells were resuspended in 1/100 volume of cold STE, lysed with 1% Triton X-100, and incubated at 37° C. for 5–10 minutes for autolysis. After the addition of 1% SDS, the cells were swirled in water bath at 50–60° C. for 5 min. RNase (100 μg/ml) and proteinase K (50 μg/ml) were added sequentially with incubations of 2 hours and 1 hours, respectively. The cells were extracted twice with one volume of phenol/chloroform and once with one volume of chloroform and the supernatant was collected for ethanol precipitation. The precipitate was washed twice with 70% ethanol, and the pellet was collected and resuspended in TE (10 mM Tris-HCl pH 8.0, 1 mM EDTA) or water as required.

The plasmid library DNA was extracted by polyethylene glycol precipitation procedure (Kreig. P. and Melton. D. 1985 supra), from pooled *E. coli* transformants and used to transform CP 1200, the parent pneumococcal strain following the method that was obtained from Dr. Morrison, University of Illinois at Chicago. For pneumococcal transformation, frozen pneumococcal competent cells were thawed on ice and to 100 μl of these competent cells, 200 ng to 1000 ng of plasmid library was added in a separate eppendorf tube. This tube was incubated at 37° C. in a water bath for about 25 min to 35 min and the mixture was diluted ¹⁄₁₀ in CAT medium and incubated further for about 1–1.7 hrs. Following the final incubation, the mixture was plated by overlay procedure (method was obtained from Dr. Morrison University of Illinois at Chicago). The overlay procedure involved pouring four different layers of agar (THB or CAT) in a small petri dish as follows: a) first or base layer: 3 ml of agar; b) second or cells' layer: mixture of 1.5 ml of agar and 1.5 ml of broth containing required concentration of bacterial cells; c) third layer: 3 ml of agar; 4) fourth layer or top layer: 3 ml of agar containing 4× required concentration of antibiotic (erythromycin, at 0.05 µg/ml×4=6 µg/ml). The plates were incubated at 37° C. Individual transformants were transferred by stab inoculation to individual wells of microtitre plates containing 100 µl of THB and erythromycin (0.05 µg/ml). The recovered transformants in microtitre plates were diluted 1:10 in SMP medium and grown until early log phase, and screened for their ability to degrade C3 by ELISA.

Spontaneous excision of recombinant plasmids occur in these kind of pneumococcal mutants with low frequency and therefore, chromosomal DNA preparations of these mutants often include low levels of plasmid DNA (Pearce B J., et al., *Mol. Microb.* 9(5):1037–1050, 1993). Electroporation of *E. coli* is a highly efficient way of isolating the plasmid constructs in *E. coli* for further study. Chromosomal DNA (100 ng–200 ng in a final volume of 2 µls) from the individual pneumococcal mutants of interest was electroporated into *E. coli* DH5 α MCR competent cells to obtain *E. coli* transformants with recombinant plasmids. One of the recovered recombinant plasmids (pLSN4a) (see Table 2) was introduced back into wild type CP 1200 pneumococcal strain by transformation. The transformant SN4-4G was again evaluated for its C3 degrading activity by ELISA.

DNA fragments were analyzed by horizontal electrophoresis in agarose gels (0.5% to 1.0%) with Tris-borate EDTA (TBE) buffer or Tris-acetic acid EDTA (TAE) buffer (Sambrook, J. E. Fritsch and T.Maniatis.1989). One kb ladder from Gibco BRL or Hindi III or Hind III/EcoRI digested lamda DNA from Boehringer Mannheim, was employed as a molecular weight standard.

Restriction endonucleases, calf intestinal phosphatase, T4 DNA ligase, from Gibco BRL Life Technology, Grand Island, N.Y., Boehringer Mannheim, Indianapolis, Id., Promega Corp., Madison, Wis., Bethesda Research Laboratories, Gaithersburg, Md., or New England Biolabs., Inc., Beverly, Mass., were used as described by the manufacturers' instructions.

DNA fragments were analyzed by Southern hybridization. DNA was transferred from gels to MSI Magnagraph nylon membranes (Micron Separations, Inc., Westboro, Mass.) for hybridization and detection using Genius nonradioactive DNA labeling and detection kit (Boehringer Mannheim Biochemicals, Indianapolis, Ind.) following the instructions provided with the kit. Chromosomal or plasmid DNA either from the pneumococcal or *E. coli* culture was isolated as described in earlier sections. About 100 ng–400 ng of each sample was digested with required restriction enzymes and run on 0.7% agarose gel, transblotted onto Magnagraph-nylon membrane overnight. The rest of the procedure was performed as instructed by the manufacturer.

Bacterial strains and plasmids used in this example and the examples that follow are summarized in Table 2 below.

TABLE 2

Bacterial Strains and plasmid constructs

| Host strains | Plasmids or constructs | recovered recombinant plasmids[a] in *E. coli* | Strain or transformant designation (with plasmids) | Plasmid or construct designation and varieties |
|---|---|---|---|---|
| *E. coli* DH5 α MCR | pVA 891 plasmid | | DH-pVA89 | pVA 891 |
| *E. coli* DH5 α MCR | | pVA891::insert 3 | LSN3 | pLSN3 |
| *E. coli* DH5 α MCR | | pVA891::insert 4 | LSN4 | pLSN4 |
| *E. coli* DH5 α MCR | | pVA891::insert 5 | LSN5a | pLSN5 |
| *E. coli* DH5 α MCR | | pVA891::insert $6_{a-b}$ | LSN$6_{a-b}$ | pLSN$6_{a-c}$ |
| *E. coli* DH5 α MCR | pVA891::ORF3a** | | DH-pVA/ORF3a** | pVA-ORF3a** |
| *E. coli* DH5 α MCR | pET 28 (+)::ORF3* | | DH-pET/ORF3 | pET-ORF3 |
| *E. coli*, BL 21 DE3 | pVA 891 plasmid | | BL-pVA891 | pVA 891 |
| *E. coli*, BL 21 DE3 | pLSN4 | | BL-pLSN4 | pLSN4 |
| *E. coli*, BL 21 DE3 | pET28 (+)::ORF3* | | BL-pET/ORF3* | pET-ORF3* |

| Pneumococcal mutants | Integrated recombinant plasmid[a] | mutants' designation | recovered recombinant plasmids'designation |
|---|---|---|---|
| *S. pneumoniae* CP 1200 | pVA891::insert 3 | SN3 | pLSN3 |
| *S. pneumoniae* CP 1200 | pVA891::insert 4 | SN4 | pLSN4 |
| *S. pneumoniae* CP 1200 | pVA891::insert 5 | SN5 | pLSN5 |
| *S. pneumoniae* CP 1200 | pVA891::insert $6_{a-b}$ | SN6 | pLSN6a-c |
| *S. pneumoniae* CP 1200 | pLSN4 | SN4-4G | pLSN4-4G |
| *S. pneumoniae* CP 1200 | PVA891::ORF3a** | SN4-S10 | |

[a]These were constructed with random chromosomal fragments of pneumococcal strain CP 1200, ligated to the EM[r] determinant shuttle vector pVA891 and were used to transform CP1200 for the purpose of Insertion-Duplication Mutagenesis.
[b]The integrated plasmids were recovered in *E. coli* from the pneumococcal mutants of interest as described in the text. See table 3 for details for different varieties of recovered recombinant plasmids from each of pneumococcal mutant.
*cppA gene.
**620 bp, and internal fragment of cppA gene.

EXAMPLE 2

Identification of Mutants with altered C3-degrading Activity

Individual pneumococcal transformants were screened by ELISA for their altered C3 degrading activity. The pneumococcal transformants were grown individually in THB in the presence of erythromycin (0.05 µg/ml) in microtitre plates up to log phase and diluted 1/0 in SMP medium (0.05 µg of erythromycin/ml). The SMP bacterial cultures were grown up to log phase and incubated with C3 (0.83 µg of C3/ml of culture) for 2–4 hrs. After incubation with C3, 100 µls of each individual transformant was transferred to an ELISA binding plate and incubated overnight at 4° C. The plates were washed with PBS (10 µM phosphate buffer saline+ 0.05% Tween-20) three times. 100 µl of HRP-conjugated goat polyclonal antibody specific to human complement C3 (1:10000 dilution of 48 mg/ml) was added to each well and the plates were incubated for 1–2 hrs at 37° C. Each microtitre plate was washed with PBS as described above. 100 μl of 30% OPD (12 mg of O-Phenylenediamine (Zymed, South San Francisco, Calif.) in 30 ml of Citrate buffer (200 mM $Na_2HPO_4$ and 100 mM citric acid-pH 5.0), and 12 μl of 30% $H_2O_2$) was added to each well and the plates were incubated for 30 min in dark. The reaction was stopped by the addition of 50 μls of 2.5M $H_2SO_4$ to each well. The amount of undegraded C3 left in the samples was detected by HRP-conjugated goat polyclonal antibody specific to human complement C3. The assay was standardized so that wells containing undegraded C3 had an O.D. 490= ~1.0. Wells with degraded C3 had reduced optical density readings resulting from decreased binding of anti-C3 antibodies. The optical densities of the mutant and parent strains were compared to that of negative controls (medium with different concentrations of C3) to calculate the percent of C3 degrading activities. There were four mutants, SN3, SN4, SN5 and SN6, with elevated C3 degrading activity (2.2 fold-Table 3) compared to the activity of their parent strain CP1200. This finding was confirmed later by Western immunoblotting for the pneumococcal mutant SN4. SN4-S10 (disrupted cppA gene) were also mutants of CP1200 with reduced C3 degrading activity.

TABLE 3

ELISA results for C3 degradation by parent and hyper active mutants of pneumococcal strains

| strains each sample or controls | ELISA reading at 490 nm | *Percentage of C3 degraded in |
|---|---|---|
| **negative control | 0.608 | 0% |
| CP1200 (parent) | 0.30 | 51% |
| SN3 (mutant) | 0.20 | 67.2% |
| SN4 (mutant) | 0.162 | 73.4% |
| SN5 (mutant) | 0.23 | 60.0% |
| SN5 (mutant) | 0.23 | 60.0% |

*average of minimum of 4 individual expts. conducted at different times
**negative sample is medium only (THB or SMP) with C3 and without bacterial cells Immunoblotting was performed using ECL Western blotting protocols (Amersham Life Sciences, Arlington Heights, Ill.). The pneumococcal mutants or *E. coli* cultures with or without plasmids were grown from freezer stock cultures, in THB or LB up to log phase and incubated with C3 (0.83 μg of C3/ml) for 2–4 hrs, the cultures were spun down (2,500 rpm for 15 min RT or 4° C.) and the supernatants were collected. The optical densities of the cultures were carefully monitored and samples were equalized before being subjected to incubation with C3. Equal amounts of all collected supernatants containing undegraded C3 were applied to 7.5% or 10% SDS-PAGE gels under reducing conditions. The gel was transblotted to nitrocellulose membrane (75 volts; 4° C.) for 1 hr. Proteins were transferred in this example and in subsequent examples from gels to nitrocellulose membranes using a Hoeffer transfer apparatus in Towbin buffer (3.03 g Tris, 14.4 g glycine and 200 ml Methanol in 1 liter volume pH.8.3; Towbin et al. (1979) *PNAS:*4350–4354) for 1 hr at 70 volts or gels were stained with 0.125% Coomassie Brilliant Blue R-250 (Pierce, Rockford, Ill.) made in 50% Methanol and 10% Acetic acid.

The blot was incubated in 10% skim milk (skim milk powder) for 1 hr (room temperature) or overnight (4° C.) with gentle shaking. The blot was washed in TTBS (0.1% Tween, 20 mM Tris, 137 mM Saline Buffer) several times and incubated with a 1:1000 dilution of HRP-conjugated goat antihuman C3, polyclonal antibody, IgG fraction (ICN Pharmaceuticals/Cappel, Costa Mesa, Calif.) made in 3xTTBS+3% BSA for 1 hr with gentle shaking. The incubated blot was washed again several times in TTBS and incubated for one minute in chemiluminescent reagents (1:1 ratio of 2xluminol/Enhancer and 2xstable peroxide solutions, Pierce. Rockford, Ill.). This blot was exposed to films for 5 sec to several seconds in the dark and the films were developed. The SDS-PAGE gels always contained pre-stained high molecular weight markers (Bethesda Research laboratories, life Sciences, Grand Island, N.Y.) ranging from 200 kd to 19 kd. The washes and incubations were performed at room temperature with a gentle shaking unless stated otherwise.

Electroporation of chromosomal DNA from the hyperactive pneumococcal mutants, SN3, SN4, SN5 and SN6 into *E. coli* DH5 α MCR competent cells gave rise to *E. coli* transformants with rescued recombinant plasmids. *E. coli* DH5 α MCR transformants, LSN3, LSN4, LSN5, LSN6, LSN4G contained plasmids (Table 2 from pneumococcal mutants, SN3, SN4 SN5, SN6 and SN4-4G mutants respectively). Details of *E. coli* strains containing different constructs are listed in Table 2 (supra). Restriction analysis (Hind III) revealed that the inserts were indeed recombinant plasmids. Different sizes of recombinant plasmids were obtained from each hyperactive pneumococcal mutant. Recombinant plasmids, pLSN3 and pLSN4 recovered from mutants SN3 and SN4 were the same size (~7.8 kb) and their insert size was ~2.4 kb. The size of the insert of an ~11 kb recombinant plasmid, pLSN5, obtained from the pneumcoccal mutant SN5 was about 5.6 kb. The fourth pneumococcal mutant, SN6, gave two different, ~6.5 kb and ~10.5 kb recombinant plasmids, $pLSN6_a$ and $pLSN6_b$, which had inserts of 1.1 kb and 5.1 kb respectively. These pneumococcal mutants were also examined by southern hybridization. The hyperactive pneumococcal mutant SN4 was chosen for further studies of C3 degradation and therefore, the recombinant plasmid pLSN4 which was rescued from the mutant SN4 was subjected to a full investigation.

Plasmid pLSN4 was used as a probe against EcoRI digested chromosomal DNA samples of the pneumococcal mutants and this confirmed the integration of the vector+ insert (pLSN4) in the mutants SN3 and SN4. Both SN3 and SN4 hyperactive mutants included two hybridizing fragments of sizes ~2.2 kb and ~5.8 kb which were also present in parent strain CP1200. There were two other hybridizing vector/insert junction fragments at ~4.2 and ~3.5 and these two together gave a total of ~7.8 kb (pLSN4 is ~7.8 kb). These two bands were also present in the EcoRI digested pLSN4 DNA sample. Both insert and vector had EcoRI sites and represented recombinant plasmid. The pattern of the other hyperactive mutants, SN5 and SN6, suggested that these mutants may have had different inserts in their integrated recombinant plasmids.

The same plasmid pLSN4 was used to retransform the parent pneumococcal strain CP1200 to confirm its involvement in hyperactivity. As expected, the obtained mutant SN4-4G (Table 2) reproduced the phenotype of enhanced C3 degradation.

EXAMPLE 3

Isolation and Identification of C3-degrading Gene

Double stranded DNA sequence analysis was performed on the insert part of the recombinant plasmid pLSN4. Since this insert was associated with C3 degrading hyper-activity, we expected to see insertion either in regulatory region of the corresponding gene or duplication of the gene; however, there was no indication of insertion in a regulatory region on the basis of the protein data base search. This suggested the possibility of gene duplication. There were three full open reading frames (ORFs) and one partial open reading frame with no significant homology between the derived amino acid sequences of the above ORFs and the proteins as provided in searches of GenBank, Blast and SwissProt databases. Preliminary data (Cathryn A S., et al., *J. Inf Dis.* 170:600–608, 1994) suggested that the C3 degrading proteinase might be cell wall associated (exported protein) and therefore, we looked for the presence of a signal sequence, a proline rich domain or a LPXTG motif. None of the four ORFs had these sequence patterns and we chose ORF3, the largest ORF for further analysis.

Double-stranded DNA of plasmid pLSN4a was prepared using CsCl gradient/ethidium bromide isolation and used as a template. Oligonucleotide primers were synthesized using an applied Biosystems 391 automated synthesizer, by Gibco BRL, or by Oligo 1000M DNA synthesizer (Beckman Instruments Inc. La Brea, Calif.) Using the dideoxy chain terminator method (Sanger F., et al. *Proc. Natl. Acad Sci.* (USA) 82:1074–1078, 1977) and employing Sequenase 2.0 (U.S. Biochem) and [$\alpha$-$^{35}$S] dATP (Amersham life Sciences, Arlington Heights, Ill.) sequencing was done with an apparatus: 20110 Macrophor Electrophoresis unit (LKB Bromma) as indicated by Sequenase version 2.0 (Amersham life sciences).

Figure 3:
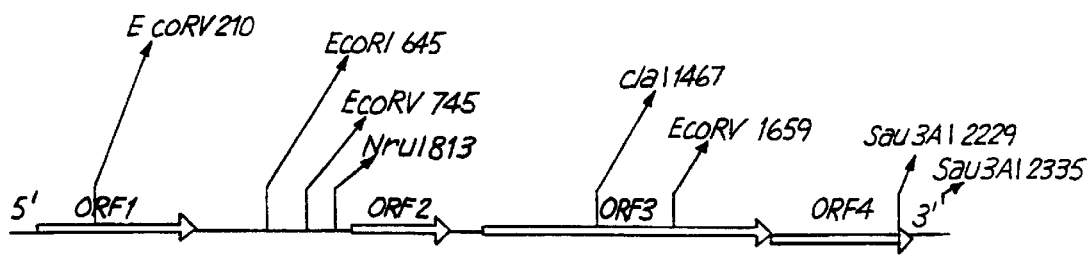
FIG. 3 is a diagram of the restriction analysis of an insert from an insertion duplication mutant of this invention.

The insert (see FIG. 3) in the recombinant plasmid pLSN4, recovered from the hyper active pneumococcal homologous-recombinant mutant SN4 seemed to have restriction sites for Hinc II, Nru I, EcoR I, Cla I, EcoR V and Hpa I out of about 20 enzymes tested and this data correlated with the sequence data.

After reviewing the sequencing data, an internal fragment, 620 bp, of the cppA gene (ORF3 of the insert) was generated by gene amplification (see Table 4 for primers) with overhangs containing Hind III restriction sites. This fragment was subcloned into Hind III sites in the vector pVA891, electroporated into *E. coli* and tested for the presence of the insert. Finally, this subclone was transformed into wt CP1200 pneumococcal competent cells to inactivate the original cppA gene in the wild type CP 1200.

DNA amplifications were carried out using a Hybaid Omnigene machine with primers (see Table 4 for primers' sequences and amplification cycle conditions) complimentary to the 5' and 3' ends of the required DNA fragments. All the primers were constructed to include a restriction site on both ends. The amplification reaction (final volume 0.1 ml volume) utilized 10 μl of 10×vent buffer (final concentration, 1× contains: 10 mM KCl, 10 mM (NH$_4$)SO$_4$, 20 mM Tris-HCl (pH 8.8 at 25° C.), 2 mM MgSO$_4$, 0.1% triton X-100), 4 μls of 100 mM MgSO$_4$ (final concentration 4 mM), 3 μl of 10 mM dNTP s (final concentration 300 μM), 50 ng template, 1 μM primers and 1 μl of 2000 units/ml of vent polymerase (final concentration 2 units; enzyme was supplied in 10 mM KCl, 0.1M EDTA, 10 μM Tris-HCl (pH 7.4), 1 mM DTT, 0.1% Triton X-100) in a final volume of 100 μl with water. Vent buffer, Vent polymerase enzyme and MgSO$_4$ were purchased from New England Biolabs, MA, and dNTPs were bought from Gibco BRL.

Additional sequence was generated via fluorescent sequencing using Applied Biosystems Model 373a DNA sequencer (DNA Sequencing Core Facility, Interdisciplinary Center for Biotechnology Research (ICBR), University of Florida, Gainesville, Fla.). A Robotlo Workstation (ABI Catalyst 800) and a Perkin Elmer-Cetus PEC 9600 thermocycler were used in cycle sequencing reactions. The template, an amplified gene product that represented the whole insert from plasmid pLSN4a, was cleaned directly from 0.7% agarose gel by Qiagen kit before it was used for automated sequencing. The sequencing analysis was conducted with programs (fasta, blast and other programs) available in the GCG software package.

TABLE 4

Primers' sequences and gene amplification cycle conditions

| amplified gene fragment and sizes (kb) | primers' sequence |
|---|---|
| *pLSN4 insert (~2.338 kb) | PCR-1(LSN4a-L): CAG GAA GCT TGA TCT TGA AAT TTC TAT GAC TCC (SEQ ID NO:3) |
| | PCR-1(LSN4a-R): CGA GAA GCT TGA TCC TGT CGA AAT CAA AGC AGG ACG (SEQ ID NO:4) |
| *ORF3a (~0.62 kb) | Left PCR-2: CAG GAA GCT TTG AAA CAA TTT ATA TTG AAA CCC (SEQ ID NO:5) |
| (internal fragment of cppA) | Right PCR-2: CGA GAA GCT TCA AGG AAG AAT TTT TCA GAC TTA GG (SEQ ID NO:6) |
| *ORF3 (~0.726 kb) | Left PCR-4: GGG GAA TTC CAT ATG AAT GTA AAT CAG ATT GTA CGG (SEQ ID NO:7) |
| (cppA gene) | Right PCR-4: CGC CGC GGA TCC TCA TAC TTC TTC AAA CCA CAA TTC (SEQ ID NO:8) |

| amplification cycle conditions | pLSN4 insert (~2.338 kb) | ORF3a (~0.62 kb) | ORF3 (~0.720 kb) |
|---|---|---|---|
| Denaturing | 98° C., 3 min, one cycle | 98° C., 3 min, one cycle | 98° C., 3 min, one cycle |
| Denaturing | | 94° C., 30 sec ⎫ | 94° C., 30 sec ⎫ |
| Annealing | | 53° C., 30 sec ⎬ 3 cycles | 59° C., 30 sec ⎬ 3 cycles |
| Extension | | 72° C., 45 sec ⎭ | 72° C., 54 sec ⎭ |
| Denaturing | 94° C., 30 sec ⎫ | 94° C., 30 sec ⎫ | 94° C., 30 sec ⎫ |
| Annealing | 55° C., 30 sec ⎬ 5 cycles | 53° C., 30 sec ⎬ 5 cycles | 59° C., 30 sec ⎬ 5 cycles |
| Extension | 72° C., 45 sec ⎭ | 72° C., 45 sec ⎭ | 72° C., 45 sec ⎭ |
| Finishing hold | 72° C., 5 min, one cycle | 72° C. 5 min, one cycle | 72° C. 5 min, one cycle |

*pLSN4, a recombinant plasmid recovered from the hyper active pneumococcal mutant SN4 (see previous tables and text); it was fully sequenced; ORF3, designated cppA is one of the open reading frames of the insert that was present in the pLSN4 and encoded C3 degrading proteinase; ORF3a is an internal part of the cppA (ORF3)gene which was used to disrupt the cppA (ORF3) gene in the parent pneumococcal strain CP1200.

EXAMPLE 4

C3-degrading Protein Isolation and Studies

Log phase cultures of hyperactive mutants and their parent strains were incubated with C3 for 2–4 hrs and the culture supernatants were run on 7.5% SDS-Page gels under reducing conditions and were checked for their increased C3 degrading activity by immunoblotting with HRP-conjugated polyclonal antibody to C3. This experiment demonstrated that mutants SN4 and SN4-4G (obtained by retransformation of CP 1200 with the recombinant plasmid pLSN4 rescued from SN4) were more active than their parent strain CP 1200 in C3 degradation. Both α and β chains C3 were almost completely degraded by the mutants after 4 hours incubation whereas the degradation was incomplete for the parent strain. The CppA protein appeared to preferentially degrade the C3 α chain.

A 620 bp internal portion of the cppA gene was ligated into Hind III site of pVA 891 and the construct was transformed into CP 1200 competent cells. The obtained transformant was tested for its ability to degrade C3. The ORF3 mutant was found to have a poor activity. The α chain of the C3 molecule was degraded and the β-chain was less degraded, by SDS-PAGE and western blotting analysis in comparison with its parent strain CP 1200. The reduced activity rather than a complete absence of activity in the mutant indicated that the potential for the presence of another fully functional gene encoding another C3 degrading proteinase in the mutant.

The entire cppA gene was amplified and cloned into Nde I and Bam H I sites of pet-28b(+) (Novagen, INC. Madison, Wis.) and the gene was incorporated with a His-Tag in its N-terminus region. The entire gene was positioned in the vector in frame as confirmed by sequence analysis. The plasmid construct was transformed into E. coli DH5 α MCR strain for stabilization and the presence of the insert was verified before the vector and insert were transformed into E. coli BL 21 D3 (Novagen) protease deficient strain for expression. The colonies containing the plasmid constructs were selected on LB medium containing kanamycin (30 μg/ml).

Protein was isolated according to the Pet System manual (Madison, Wis.) for small scale or large scale preparations. The BL 21 DE3 strain containing the construct (pet 28b(+)::ORF3 (cppA gene) was induced by IPTG and the expressed protein, CppA, was solubilized. For solubilization, the induced bacterial cultures were centrifuged and the pellet was resuspended in TES (50 mM Tris; 1 mM EDTA; 100 mM NaCl). The resuspension was sonicated (6×0.15 sec pulses at a high output setting: about 50 watts) on ice and spun down to collect the pellet. The pellet was washed in TES (50 mM Tris; 1 mM EDTA; 100 mM NaCl) twice and finally the pellet was treated with 6 mM G-HCl+1 mM DTT+1% Tween-20 for 3 hrs at 4° C.

The solubilized protein was diluted 1:10 in TTS (1% Tween, 50 mM Tris, 0.7M NaCl) and dialyzed against TTS (1% Tween, 50 mM Tris, 0.7M NaCl) to remove Guanidine-HCl, DTT and EDTA. The dialysed CppA protein was purified by Nickel column chromatography using the Pet system manual instructions (Novagen, INC. Madison, Wis.). Nickel column (2.5 ml) was poured and after removal of Guanidine-HCl, DTT and EDTA, the expressed His-Tagged CppA protein was applied to the Nickel column for purification. The eluted fractions were tested for His-Tagged-CppA protein by 10% SDS-PAGE gel and Coomassie Brilliant Blue R-250 staining. The protein was kept on ice at 4° C. or frozen in small aliquots at −80° C. until required.

The CppA protein (about 600 ng per ml of the reaction mixture) was incubated with human complement C3 (0.83 μg of C3 per ml of the reaction mixture) for 4 hrs at 37° C. in the presence of PBS and a negative control without protein was simultaneously set up. The samples were analyzed by 7.5% or 10% SDS-PAGE gel under reducing conditions and western-blotting (ECL Western blotting protocols—Amersham Life Sciences, Arlington Heights, Ill.).

As described above, the PCR product of the whole ORF3 gene was subcloned into pet vector pET28b(+) (Novagen, Madison, Wis.) with a His-tag in the amino terminus position and the construct was introduced into protease deficient strain E. coli BL 21 DE3 (Table 2) after it was stabilized in E. coli DH5α MCR. The E. coli BL 21 DE3 with the construct was subjected to induction by IPTG. Total cell protein extracts of the induced and uninduced cultures were tested. The expressed His-tagged ORF3 protein (~29 kd) was identified in the insoluble fraction of the induced protein sample on 10% SDS-Page gel.

The following reagents were used for solubilization for 3 hrs at 4° C. or 1 hr at room temperature: TES (50 mM Tris, 1 mM EDTA, 1M NaCl; (b) 6 mM G-HCl+1 mM DTT; (c) 6 mM G-HCl+1 mM DTT+1% Tween 20; (d) 6 mM G-HCl+1 mM DTT+1% Triton X-100. Both "c" and "d" treatments made the expressed protein soluble as it was observed on 10% SDS-PAGE gel. The treatment with "c" reagent was chosen for subsequent large scale preparations. The solubilized protein was dialysed followed by purification through the nickel column and examined for its function against C3.

For SDS-PAGE gels used in this example and above, total cell proteins or soluble or insoluble protein fractions were extracted according to Pet-system manual (Madison, Wis.). The proteins were separated by SDS-PAGE gels (7.5% or 10% or 15% resolving gel and 4.5% stacking gel) in the discontinuous system of Laemmli (Laemmli, U. K., Nature 227:680–685, 1970). Briefly, samples were combined with loading buffer (final concentration in samples was 7.57 mg/ml of Tris, 2% SDS, 10% Glycerol and 1.25 mg/ml of Bromphenol blue, ±5% β-mercaptoethanol) and either boiled 5 min or loaded directly on the resolving gels. Pre-stained high molecular weight standards (Protein markers (kd): lysozyme, 14,300; β-lactoglobulin, 18,400; carbonic anhydrase, 29,000; ovalbumin, 43,000; bovine serum albumin, 68,000; phophorylase B, 97,400 myosin, 200,00 (Bethesda research laboratories, life sciences, Grand Land, N.Y.) were included on the gels. The large SDS-PAGE gels were electrophoresed at 15 mA for 14 hrs or 10 mA for 20 hr. Mini gels were electrophoresed around 2–3 hrs at a constant voltage (100–150 volts).

The expressed protein was incubated with C3 and the amount of C3 present was assessed by Western immunoblotting.

Immunoblotting analysis suggested that the samples that contained the expressed protein degraded C3 molecules. The undegraded C3 was detected by polyclonal antibodies specific to human complement C3 and this was clearly seen on the developed film in the case of the negative sample. Both α and β chains of C3 molecules were seemed to be susceptible to the activity of the ORF3 protein in comparison with the negative control which did not contain any ORF3 protein; however, the α chain was almost completely degraded while the β chain was partially degraded in the ORF3 samples.

EXAMPLE 5

Conservation of the C3-degrading Gene in Clinical Isolates

To examine the conservation of the gene cppA, an internal fragment of cppA was used as a probe to determine the presence of gene cppA in EcoRI digested genomic DNA of different clinical (serotypes) of pneumococcal isolates by southern hybridization. In the same experiment, the pneumococcal parent CP1200 and the hyperactive mutants SN4 and SN4-4G (both mutants containing the same plasmids-see Table 2) were also included to confirm the duplication of the cppA gene in the mutants. Southern hybridization was performed using non-radioactive DIG labeled internal fragment of the gene as a probe. The clinical isolates, type1, type3, type 14F and virulent type 23F showed a hybridized band of about 2.3 kb which was also present in the control pneumococcal strain CP1200 and in the SN4 mutants. This common band indicates that the cppA gene was present in all isolates tested. The SN4 mutants also contained a second band with a size of about 3.5 kb indicating the presence of a gene duplication. The 3.5 kb size is consistent with the observation that plasmid pLSN4 has two restriction endonuclease recognition sites for EcoRI, one in the insert region and a second in the vector. Hence the restriction digestion with EcoRI produces two fragments of about 4.175 kb (3.531 kb of vector+0.649 kb of insert) and 3.539 kb (~1.67 kb form insert+about 1.869 kb from vector) from the recombinant plasmid. The cppA gene was located on the 1.67 kb portion of the insert and hence the ~3.539 kb restricted fragment of the recombinant plasmid contained the cppA gene and only this band would hybridize to the probe which was an internal fragment of the cppα gene; therefore, in the case of the mutants with duplicated cppA gene, the second hybridized band at ~3.5 kb represented the duplicated cppa gene.

What is claimed is:

1. An isolated and purified protein comprising at least an 80% sequence identity of SEQ ID NO:2 and that binds human complement protein C3.

2. The protein of claim 1 wherein the protein is isolated and purified from *S. pneumoniae*.

3. The protein of claim 1, wherein the protein is a recombinant protein.

4. The protein of claim 1 having a molecular weight as determined on a 10% polyacrylamide gel of between about 24 kDa to about 34 kDa.

5. The protein of claim 4, wherein the protein is isolated and purified from S. pneumoniae.

6. The protein of claim 4 wherein the protein is a recombinant protein.

7. The protein of claim 4 wherein the protein degrades human complement protein C3.

8. A peptide comprising at least 15 sequential amino acids from the protein of claim 1.

9. A composition comprising the peptide of claim 8.

10. The composition of claim 9, further comprising an adjuvant.

11. A composition comprising the protein of claim 1.

12. The composition of claim 11 further comprising an adjuvant.

13. An isolated and purified protein comprising SEQ ID NO:2.

14. A composition comprising the protein of claim 13.

15. The composition of claim 14 further comprising an adjuvant.

16. A peptide comprising at least 15 sequential amino acids set forth in SEQ ID NO:2, wherein said peptide binds human complement protein C3.

17. A composition comprising the peptide of claim 16.

18. The composition of claim 17 further comprising an adjuvant.

19. A protein comprising amino acids 1–50 of SEQ ID NO:2.

20. A composition comprising the protein of claim 19.

21. The composition of claim 20 further comprising an adjuvant.

22. An isolated and purified protein that binds human complement protein C3 and wherein nucleic acid encoding the protein hybridizes to SEQ ID NO:1 under hybridization conditions of 6×SSC, 5×Denhardt, 0.5% SDS, and 100 µg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes.

23. A composition comprising the protein of claim 22.

24. The composition of claim 23 further comprising an adjuvant.

25. An immunogenic composition comprising an isolated and purified polypeptide comprising SEQ ID NO:2.

26. The composition of claim 25 wherein the polypeptide is isolated and purified from S. pneumoniae.

27. The composition of claim 25 further comprising at least one other immune stimulating peptide, polypeptide or protein from S. pneumoniae.

28. An isolated nucleic acid fragment that hybridizes to SEQ ID NO:1 under hybridization conditions of 6×SSC, 5×Denhardt, 0.5% SDS, and 100 µg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes, wherein said isolated nucleic acid fragment encodes a polypeptide that binds human complement protein C3.

29. The nucleic acid of claim 28 isolated from an S. pneumoniae genome.

30. The nucleic acid of claim 28 wherein the polypeptide degrades human complement C3.

31. The nucleic acid fragment of claim 28 wherein the nucleic acid fragment encodes a polypeptide that does not degrade human complement C3.

32. The nucleic acid of claim 28 in a nucleic acid vector.

33. The nucleic acid of claim 32 wherein the vector is an expression vector.

34. An isolated host cell comprising the nucleic acid vector of claim 32.

35. The cell of claim 34 wherein the cell is a bacterium or a eukaryotic cell.

36. An isolated host cell comprising the isolated nucleic acid of claim 28.

37. A method of expressing a polypeptide that binds to human complement protein C3, the method comprising culturing a recombinant host cell transformed with an isolated nucleic acid fragment of claim 28 under conditions suitable for expression of a polypeptide and recovering the polypeptide so expressed.

38. An isolated nucleic acid fragment comprising the nucleic acid sequence gctcccagtatgcgtactcgtaaggtagagggaagaaaaaaactagctag (SEQ ID NO:9), wherein said isolated nucleic acid fragment encodes a polypeptide that binds human complement protein C3.

39. A method for producing an immune response to S. pneumoniae in an animal comprising the steps of:

administering a composition comprising a polypeptide comprising SEQ ID NO:2 to a mammal; and obtaining an immune response to the polypeptide in said animal.

40. The method of claim 39 wherein the immune response is a B cell response.

41. The method of claim 39 wherein the immune response is a T cell response.

42. The method of claim 39 wherein the composition further comprises at least one other protein from S. pneumoniae.

43. A bacteria comprising a nucleic acid comprising an insertional mutation, wherein said mucleic acid encodes a protein of claim 1.

44. The bacteria of claim 43 wherein the insertional mutation comprises an insertional duplication mutation.

45. An isolated and purified of about 24 kDa to about 34 kDa from Streptococcus pneumoniae that binds to human complement C3.

46. An isolated nucleic acid fragment comprising the nucleic acid sequence of SEQ ID NO:1.

47. The isolated nucleic acid fragment of claim 46 wherein the nucleic acid fragment encodes a protein that binds human complement C3.

48. An isolated RNA fragment transcribed from a double-stranded DNA sequence comprising SEQ ID NO:1.

49. An isolated nucleic acid fragment that encodes a polypeptide having at least an 80% sequence identity with SEQ ID NO:2 and binds human complement protein C3.

50. The isolated nucleic acid fragment of claim 49, said isolated nucleic acid fragment encoding a polypeptide comprising SEQ ID NO:2.

* * * * *

UNITED STATES PATENT AND TRADEMARK OFFICE
CERTIFICATE OF CORRECTION

PATENT NO. : 6,676,943 B1
DATED : January 13, 2004
INVENTOR(S) : Hostetter et al.

It is certified that error appears in the above-identified patent and that said Letters Patent is hereby corrected as shown below:

<u>Title page, Item [54] and Column 1, lines 1-2,</u>
Title, delete "HUMAN COMPLEMENT C3-DEGRADING PROTEIN FROM STREPTOCOCCUS PNEUMONIAE" and insert -- HUMAN COMPLEMENT C3-BINDING PROTEIN FROM STREPTOCOCCUS PNEUMONIAE --

<u>Title page,</u>
Item [75], Inventors, delete "Mendota Heights" and insert -- Eagan --
OTHER PUBLICATIONS, "Gordon et al.," reference, delete "Tiolester" and insert -- Thiolester --; and "Nakamura et al." reference, delete "fo" and insert -- of --

<u>Column 4,</u>
Line 23, delete "SEQ ID NO:9" and insert -- (SEQ ID NO: 9) --

<u>Column 24,</u>
Line 14, delete "cppa" and insert -- cppA --

<u>Column 30,</u>
Line 47, after "purified" insert -- protein --

Signed and Sealed this

First Day of June, 2004

JON W. DUDAS
*Acting Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 726 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGAATGTAA ATCAGATTGT ACGGATTATT CCTACTTTAA AAGCTAATAA TAGAAAATTA      60

AATGAAACAT TTTATATTGA AACCCTTGGA ATGAAGGCCT TGTTAGAAGA ATCGGCCTTT     120

CTGTCACTAG GTGACCAAAC GGGTCTTGAA AAGCTGGTTT TAGAAGAAGC TCCCAGTATG     180

CGTACTCGTA AGGTAGAGGG AAGAAAAAAA CTAGCTAGAT TGATTGTCAA GGTGGAAAAT     240

CCCTTAGAAA TTGAAGGAAT CTTATCTAAA ACAGATTCGA TTCATCGATT ATATAAAGGT     300

CAAAATGGCT ACGCTTTTGA AATTTTCTCA CCAGAAGATG ATTTGATTTT GATTCATGCG     360

GAAGATGACA TAGCAAGTCT AGTAGAAGTA GGAGAAAAGC CTGAATTTCA AACAGATTTG     420

GCATCAATTT CTTTAAGTAA ATTTGAGATT TCTATGGAAT TACATCTCCC AACTGATATC     480

GAAAGTTTCT TGGAATCATC TGAAATTGGG GCATCCCTTG ATTTTATTCC AGCTCAGGGG     540

CAGGATTTGA CTGTGGACAA TACGGTTACC TGGGACTTAT CTATGCTCAA GTTCTTGGTC     600

AATGAATTAG ACATAGCAAG TCTTCGCCAG AAGTTTGAGT CTACTGAATA TTTTATTCCT     660

AAGTCTGAAA AATTCTTCCT TGGTAAAGAT AGAAATAATG TTGAATTGTG GTTTGAAGAA     720

GTATGA                                                               726
```

(2) INFORMATION FOR SEQ ID NO:2:

(i) SEQUENCE CHARACTERISTICS:
      (A) LENGTH: 241 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Met Asn Val Asn Gln Ile Val Arg Ile Ile Pro Thr Leu Lys Ala Asn
1               5                   10                  15

Asn Arg Lys Leu Asn Glu Thr Phe Tyr Ile Glu Thr Leu Gly Met Lys
            20                  25                  30

Ala Leu Leu Glu Glu Ser Ala Phe Leu Ser Leu Gly Asp Gln Thr Gly
        35                  40                  45

Leu Glu Lys Leu Val Leu Glu Glu Ala Pro Ser Met Arg Thr Arg Lys
    50                  55                  60

Val Glu Gly Arg Lys Lys Leu Ala Arg Leu Ile Val Lys Val Glu Asn
65                  70                  75                  80

Pro Leu Glu Ile Glu Gly Ile Leu Ser Lys Thr Asp Ser Ile His Arg
                85                  90                  95

Leu Tyr Lys Gly Gln Asn Gly Tyr Ala Phe Glu Ile Phe Ser Pro Glu
            100                 105                 110

Asp Asp Leu Ile Leu Ile His Ala Glu Asp Asp Ile Ala Ser Leu Val
            115                 120                 125

Glu Val Gly Glu Lys Pro Glu Phe Gln Thr Asp Leu Ala Ser Ile Ser
    130                 135                 140

Leu Ser Lys Phe Glu Ile Ser Met Glu Leu His Leu Pro Thr Asp Ile
145                 150                 155                 160

Glu Ser Phe Leu Glu Ser Ser Glu Ile Gly Ala Ser Leu Asp Phe Ile
            165                 170                 175

Pro Ala Gln Gly Gln Asp Leu Thr Val Asp Asn Thr Val Thr Trp Asp
            180                 185                 190

Leu Ser Met Leu Lys Phe Leu Val Asn Glu Leu Asp Ile Ala Ser Leu
            195                 200                 205

Arg Gln Lys Phe Glu Ser Thr Glu Tyr Phe Ile Pro Lys Ser Glu Lys
    210                 215                 220

Phe Phe Leu Gly Lys Asp Arg Asn Asn Val Glu Leu Trp Phe Glu Glu
225                 230                 235                 240

Val (2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CAGGAAGCTT GATCTTGAAA TTTCTATGAC TCC                                    33

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGAGAAGCTT GATCCTGTCG AAATCAAAGC AGGACG                                 36

(2) INFORMATION FOR SEQ ID NO:5:
```

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CAGGAAGCTT TGAAACAATT TATATTGAAA CCC                                       33

(2) INFORMATION FOR SEQ ID NO:6:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

CGAGAAGCTT CAAGGAAGAA TTTTTCAGAC TTAGG                                     35

(2) INFORMATION FOR SEQ ID NO:7:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GGGGAATTCC ATATGAATGT AAATCAGATT GTACGG                                    36

(2) INFORMATION FOR SEQ ID NO:8:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CGCCGCGGAT CCTCATACTT CTTCAAACCA CAATTC                                    36

(2) INFORMATION FOR SEQ ID NO:9:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GCTCCCAGTA TGCGTACTCG TAAGGTAGAG GGAAGAAAAA AACTAGCTAG                     50